(12) United States Patent
Cogan et al.

(10) Patent No.: US 7,592,332 B2
(45) Date of Patent: *Sep. 22, 2009

(54) CYTOKINE INHIBITORS

(75) Inventors: Derek Cogan, Sandy Hook, CT (US);
Daniel R. Goldberg, Redding, CT (US);
Ming-Hong Hao, Ridgefield, CT (US);
Zhaoming Xiong, Danbury, CT (US);
Ronald A. Aungst, Clifton Park, NY (US); Amy L. Davis, Schoharie, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/201,766

(22) Filed: Aug. 29, 2008

(65) Prior Publication Data

US 2009/0023701 A1 Jan. 22, 2009

Related U.S. Application Data

(60) Division of application No. 11/839,136, filed on Aug. 15, 2007, now abandoned, which is a continuation of application No. 11/119,524, filed on Apr. 29, 2005, now Pat. No. 7,285,545.

(60) Provisional application No. 60/567,693, filed on May 3, 2004.

(51) Int. Cl.
A61K 31/397 (2006.01)
A61K 31/444 (2006.01)
A61K 31/4439 (2006.01)
A61K 31/4545 (2006.01)
C07D 401/14 (2006.01)
C07D 401/02 (2006.01)

(52) U.S. Cl. .......................... 514/210.02; 514/252.18; 514/253.01; 514/333; 514/339; 544/295; 544/364; 546/256; 546/278.1

(58) Field of Classification Search ............ 514/210.02, 514/252.18, 253.01, 333, 339; 544/364, 544/295; 546/256, 278.1
See application file for complete search history.

(56) References Cited

U.S. PATENT DOCUMENTS 7,078,419 B2 * 7/2006 Cirillo et al. ................. 514/336
2005/0004176 A1 1/2005 Dyckman et al.

FOREIGN PATENT DOCUMENTS

| DE | 4302051 A1 | 7/1994 |
|---|---|---|
| WO | 9632382 A1 | 10/1996 |
| WO | WO 9951580 A1 | 10/1999 |
| WO | 0024735 A1 | 5/2000 |
| WO | 0127089 A1 | 4/2001 |
| WO | 03002910 A1 | 1/2003 |
| WO | 03022820 A1 | 3/2003 |
| WO | 03030902 A1 | 4/2003 |
| WO | 03063781 A2 | 8/2003 |
| WO | 03087085 A1 | 10/2003 |
| WO | 2005016918 A2 | 2/2005 |

* cited by examiner

*Primary Examiner*—Kamal A Saeed
*Assistant Examiner*—Jason Nolan
(74) *Attorney, Agent, or Firm*—Michael P. Morris; Mary-Ellen M. Devlin; Anthony P. Bottino

(57) ABSTRACT

Disclosed are compounds of formula (I)

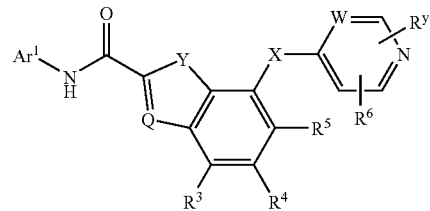

which inhibit production of cytokines involved in inflammatory processes and are thus useful for treating diseases and pathological conditions involving inflammation such as chronic inflammatory disease. Also disclosed are processes for preparing these compounds and pharmaceutical compositions comprising these compounds.

8 Claims, No Drawings

CYTOKINE INHIBITORS

APPLICATION DATA

This is a divisional application of U.S. patent application Ser. No. 11/839,136, filed Aug. 15, 2007, which is a continuation of U.S. patent application Ser. No. 11/119,524, filed Apr. 29, 2005, now U.S. Pat. No. 7,285,454, and claims benefit of U.S. Provisional Application No. 60/567,693, filed May 3, 2004, the entireties of which are incorporated herein by reference.

BACKGROUND OF THE INVENTION

1. Technical Field

This invention relates to compounds of formula (I)

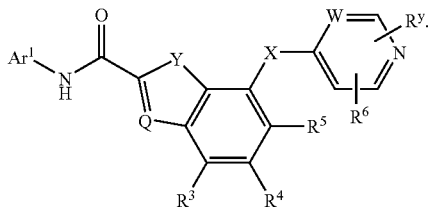

The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

2. Background Information

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28-38). Studies suggest that inflammatory changes mediated by cytokines may be involved in endothelial cell pathogenesis including restenosis after percutaneous transluminal coronary angioplasty (PTCA) (Tashiro, H., et al., 2001 March, *Coron Artery Dis* 12(2):107-13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24-5, 1997). These include the treatment of rheumatoid arthritis, Crohn's disease and ulcerative colitis (Rankin, E. C. C., et al., 1997, *British J. Rheum.* 35: 334-342 and Stack, W. A., et al., 1997, *Lancet* 349: 521-524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143). IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1a are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J. Resp. & Crit. Care Med.*, 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3-12), kidney (Lemay et al., 2000, *Transplantation*, 69, 959), and the nervous system (Mitsui et al., 1999, *Brain Res.*, 844, 192). TNFα is also a potent osteoclastogenic agent and is involved in bone resorption and diseases involving bone resorption (Abu-Amer et al., 2000, *J. Biol. Chem.*, 275, 27307).

It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867). IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol. Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med. Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64).

Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and post-menopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 Suppl 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNFα anatagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15 90(2)95-101; Shock 1998 Sep. 10(3):160-75. p38MAP kinase pathway plays an role in *B. burgdorferi*-elicited inflammation and may be useful in treating inflammation induced by the Lyme disease agent. Anguita, J. et. al., *The Journal of Immunology*, 2002, 168:6352-6357.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

Compounds active against p38 MAP kinase can also be useful for treating various types of cancers as described in WO 03/068223.

U.S. Pat. No. 5,162,360 discloses N-substituted aryl-N'-heterocyclic substituted urea compounds which are described as being useful for treating hypercholesterolemia and atherosclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production with small molecule compounds will be beneficial in the treatment of various disease states.

It is therefore an object of the invention to provide compounds of formula (I)

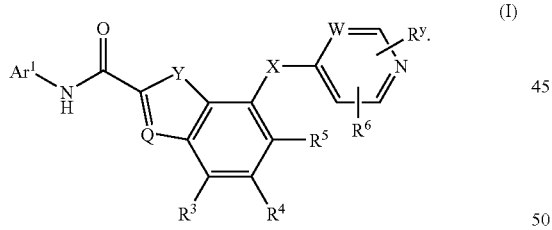

It is a further object of the invention to provide methods for treating cytokine mediated diseases and pathological conditions involving inflammation such as chronic inflammatory disease, using the novel compounds of the invention.

It is yet a further object of the invention to provide pharmaceutical compositions and processes of preparation of the above-mentioned novel compounds.

DETAILED DESCRIPTION OF THE PREFERRED EMBODIMENTS

In a broad generic aspect of the invention there is provided a compound of the formula (I)

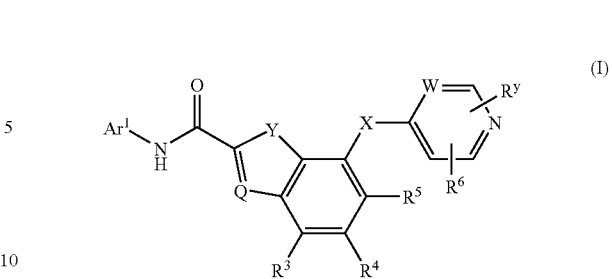

wherein:
$Ar^1$ is chosen from rings (i), (ii) and (iii) below:

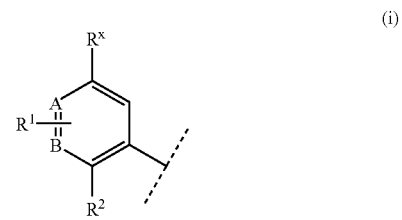

wherein one of A or B is nitrogen and the other is carbon, $R^1$ is covalently attached to either A or B, and when nitrogen is $N—R^1$ the double bond between A and B is not present;

$R_1$ is chosen from hydrogen, $NO_2$, $—N(R^c)_2$, $J-C(O)—N(R^c)—$, $J-S(O)_m—N(R^c)—$, or $R^1$ is chosen from $C_{1-6}$ alkyl, $C_{3-7}$ cylcoalkyl, $C_{1-5}$ alkoxyl or $C_{3-7}$ cycloalkoxyl, $C_{1-5}$ alkylthiol or $C_{3-7}$ cycloalkylthiol, $C_{1-5}$ acyl, $C_{1-5}$ alkoxycarbonyl, $C_{1-5}$ acyloxy, $C_{1-5}$ acylamino, $C_{2-5}$ alkenyl, $C_{2-5}$ alkynyl, heterocycle, heteroaryl and nitrile, each of the aforementioned where possible are optionally partially or fully halogenated or are optionally further substituted with alkylsulfonylamino, alkoxyl, amino, alkylamino, dialkylamino, hydroxyl, oxo, nitro or nitrile;

or $R^1$ is, where P can be O , $>CR^9$ or $>NR^9$

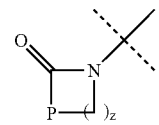

wherein z is 1 to 4, preferably 1 to 2, $R^9$ is chosen from $C_{1-6}$ alkyl, $C_{3-7}$ cylcoalkyl, $C_{1-5}$ alkoxyl or $C_{3-7}$ cycloalkoxyl, $C_{1-5}$ alkylthiol or $C_{3-7}$ cycloalkylthiol, $C_{1-5}$ acyl, $C_{1-5}$ alkoxycarbonyl, $C_{1-5}$ acyloxy, $C_{1-5}$ acylamino, $C_{2-5}$ alkenyl, $C_{2-5}$ alkynyl, heterocycle, heteroaryl and nitrile, each of the aforementioned where possible are optionally partially or fully halogenated or are optionally further substituted with alkylsulfonylamino, alkoxyl, amino, alkylamino, dialkylamino, hydroxyl, oxo, nitro or nitrile;

$R^2$ is chosen from hydrogen, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl, oxo, $C_{1-5}$ alkylS(O)$_m$— and amino optionally mono- or di-substituted by $C_{1-5}$ alkyl, aryl or aryl $C_{1-5}$ alkyl;

(ii)

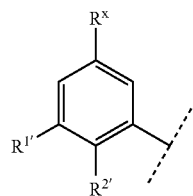

wherein
R$^{1'}$ is chosen from hydrogen, C$_{1-5}$ alkylS(O)$_m$—, C$_{1-6}$ alkyl, C$_{3-7}$ cylcoalkyl, C$_{1-5}$ alkoxyl or C$_{3-7}$ cycloalkoxyl, C$_{1-5}$ alkylthiol C$_{3-7}$ cycloalkylthiol, C$_{1-5}$ acyl, C$_{1-5}$ alkoxycarbonyl, C$_{1-5}$ acyloxy, C$_{2-5}$ alkenyl, C$_{2-5}$ alkynyl, heterocycle, heterocycleC$_{1-6}$ alkyl, heteroaryl, heteroarylC$_{1-6}$ alkyl and nitrile, each of the aforementioned where possible are optionally partially or fully halogenated or are optionally further substituted with alkylsulfonylamino, alkoxyl, amino, alkylamino, dialkylamino, hydroxyl, oxo, nitro or nitrile;

R$^{2'}$, is chosen from nitrile, C$_{1-5}$ alkylS(O)$_m$—, J-O—C(O)—O—, NH$_2$—C(O)—(CH$_2$)$_n$—, H, halogen, C$_{1-5}$ alkyl, C$_{1-5}$ alkoxy, C$_{1-5}$ alkylC$_{1-5}$ alkoxy, hydroxy, hydroxy C$_{1-5}$ alkyl and amino optionally mono- or di-substituted by C$_{1-5}$ alkyl, aryl or aryl C$_{1-5}$ alkyl;

(iii)

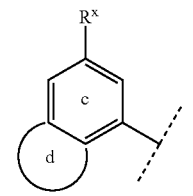

wherein c is a benzo ring fused to ring d which is a 5-7 membered heterocyclic ring;

each R$^x$ is chosen from C$_{1-6}$ alkyl or C$_{3-7}$ cycloalkyl each being optionally substituted by C$_{1-3}$ alkyl and optionally partially or fully halogenated, C$_{1-4}$ acyl, aroyl, C$_{1-4}$ alkoxy, which may optionally be partially or fully halogenated, halogen, C$_{1-6}$ alkoxycarbonyl, carbocyclesulfonyl and —SO$_2$—CF$_3$;

each J is independently chosen from C$_{1-10}$ alkyl and carbocycle each optionally substituted by R$^b$;

R$^b$ is chosen from hydrogen, C$_{1-5}$ alkyl, hydroxyC$_{1-5}$ alkyl, C$_{2-5}$ alkenyl, C$_{2-5}$ alkynyl, carbocycle, heterocycle, heteroaryl, C$_{1-5}$ alkoxy, C$_{1-5}$ alkylthio, amino, C$_{1-5}$ alkylamino, C$_{1-5}$ dialkylamino, C$_{1-5}$ acyl, C$_{1-5}$ alkoxycarbonyl, C$_{1-5}$ acyloxy, C$_{1-5}$ acylamino, each of the aforementioned are optionally partially or fully halogenated, or R$^b$ is chosen from C$_{1-5}$ alkylsulphonylamino, hydroxy, oxo, halogen, nitro and nitrile;

Q is a N or CR$^p$;

Y is >CR$^p$R$^v$, —CR$^p$=C(R$^V$)—, —O—, —N(R$^c$)— or >S(O)$_m$;

each R$^c$, R$^p$, R$^V$ and R$^y$ are each independently hydrogen or C$_{1-5}$ alkyl;

X is —CH$_2$—, —N(R$^c$)—, —O— or —S—;

W is N or CH;

each m independently 0, 1 or 2;

n is 1-4;

each R$^3$, R$^4$ and R$^5$ are independently chosen from hydrogen, C$_{1-6}$ alkyl and halogen;

R$^6$ is optionally attached at a position ortho or meta to the N atom of the indicated ring, and is chosen from a bond, —O—, —O—(CH$_2$)$_{1-5}$—, >C(O), —NH—, —C(O)—NH—, —S—, C$_{1-5}$ alkyl branched or unbranched, C$_{2-5}$ alkenyl, C$_{1-3}$ acyl, C$_{1-3}$ alkyl(OH), heterocycle selected from morpholinyl, piperazinyl, piperidinyl, pyrrolidinyl and tetrahydrofuranyl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl and isothiazolyl or aryl each alkyl, alkenyl, acyl, heterocycle, heteroaryl and aryl are optionally substituted by one to three hydroxy, oxo, C$_{1-3}$ alkyl, C$_{1-3}$ alkoxy, C$_{1-5}$ alkoxycarbonyl, —NR$^7$R$^8$ or NR$^7$R$^8$—C(O)— wherein each R$^6$ is further optionally covalently attached to groups chosen from:

hydrogen, NR$^7$R$^8$, C$_{1-3}$ alkyl, C$_{3-6}$ cycloalkylC$_{0-2}$alkyl, hydroxy, C$_{1-3}$ alkoxy, phenoxy, benzyloxy, arylC$_{0-4}$ alkyl, heteroaryl C$_{0-4}$ alkyl and heterocycle C$_{0-4}$alkyl, each above-listed heterocycle, heteroaryl and aryl group is optionally substituted by one to three hydroxy, oxo, C$_{1-4}$ alkyl, C$_{1-3}$ alkoxy, C$_{1-5}$ alkoxycarbonyl, NR$^7$R$^8$—C(O)— or C$_{1-4}$ acyl;

each R$^7$ and R$^8$ are independently hydrogen, phenylC$_{0-3}$alkyl optionally substituted by halogen, C$_{1-3}$ alkyl or diC$_{1-5}$ alkyl amino, or R$^7$ and R$^8$ are C$_{1-2}$ acyl, benzoyl or C$_{1-5}$ branched or unbranched alkyl optionally substituted by C$_{1-4}$ alkoxy, hydroxy or mono or diC$_{1-3}$ alkyl amino;

or the pharmaceutically acceptable salts and/or isomers thereof.

In another embodiment there is provided a compound of the invention as described immediately above and wherein:

if Ar$^1$ is (i) then:
R$^1$ is chosen from hydrogen, C$_{1-6}$ alkyl, C$_{3-7}$ cylcoalkyl, C$_{1-5}$ alkoxyl and nitrile, each of the aforementioned where possible are optionally partially or fully halogenated or are optionally further substituted with alkylsulfonylamino, alkoxyl, amino, alkylamino, dialkylamino, hydroxyl, oxo, nitro or nitrile;

R$^2$ is chosen from hydrogen, halogen, C$_{1-5}$ alkyl, C$_{1-5}$ alkoxy, C$_{1-5}$ alkylC$_{1-5}$ alkoxy, hydroxy, hydroxy C$_{1-5}$ alkyl, oxo, C1-5 alkylS(O)$_m$— and amino optionally mono- or di-substituted by C$_{1-5}$ alkyl, phenyl or phenyl C$_{1-5}$ alkyl;

if Ar$^1$ is (ii) then:
R$^{1'}$ is chosen from H, C$_{1-6}$ alkyl, C$_{1-5}$ alkylS(O)$_m$—, C$_{1-5}$ alkoxyl C$_{1-5}$ alkylthiol, NH$_2$—C(O)—(CH$_2$)$_n$—, heterocycle, heterocycleC$_{1-6}$ alkyl, heteroaryl and nitrile, each of the aforementioned where possible are optionally partially or fully halogenated or are optionally further substituted with alkylsulfonylamino, alkoxyl, amino, alkylamino, dialkylamino, hydroxyl, oxo, nitro and nitrile;

R$^{2'}$ is chosen from C$_{1-5}$ alkylS(O)$_m$—, J-O—C(O)—O—, C$_{1-5}$ alkyl and C$_{1-5}$ alkoxy;

or if Ar$^1$ is (iii) then:
ring d is a 5-6 membered heterocyclic ring.

In another embodiment, there are provided compounds of the formula (I) as described immediately above and wherein if Ar$^1$ is (i) then:
R$^1$ is chosen from hydrogen, C$_{1-6}$ alkyl or nitrile;
R$^2$ is chosen from hydrogen, halogen, C$_{1-5}$ alkyl, C$_{1-5}$ alkoxy, oxo or C$_{1-5}$ alkylS(O)$_m$—;

if Ar$^1$ is (ii) then:

$R^{1'}$ is chosen from hydrogen, $C_{1-6}$ alkyl, $C_{1-5}$ alkylS(O)$_m$—, $C_{1-5}$ alkoxyl $C_{1-5}$ alkylthiol, NH$_2$—C(O)—(CH$_2$)$_n$—, morpholino $C_{1-6}$ alkyl, heteroaryl chosen from pyrazole, triazole, imidazole and tetrazole, and nitrile;

$R^{2'}$ is chosen from $C_{1-5}$ alkylS(O)$_m$—, J-O—C(O)—O—, $C_{1-5}$ alkyl and $C_{1-5}$ alkoxy;

or if Ar$^1$ is (iii) then:

ring d is a 5-6 membered heterocyclic ring such that rings c and d fuse to form the following:

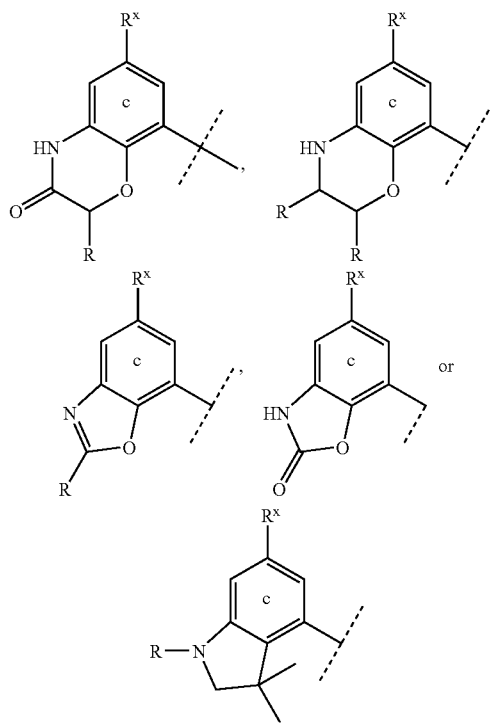

where each R is independently H or $C_{1-3}$ alkyl.

In yet another embodiment, there are provided compounds of the formula (I) as described in any of the embodiments shown above and wherein J is chosen from $C_{1-10}$ alkyl, aryl and $C_{3-7}$ cycloalkyl each optionally substituted by $R^b$;

$R^x$ is independently chosen from $C_{1-6}$ alkyl which may optionally be partially or fully halogenated, $C_{3-6}$ cycloalkyl optionally substituted by $C_{1-3}$ alkyl and optionally partially or fully halogenated, acetyl, aroyl, $C_{1-4}$ alkoxy, which may optionally be partially or fully halogenated, halogen, methoxycarbonyl, phenylsulfonyl and —SO$_2$—CF$_3$;

$R^b$ is chosen from hydrogen, $C_{1-5}$ alkyl, $C_{2-5}$ alkenyl, $C_{2-5}$ alkynyl, $C_{3-8}$ cycloalkylC$_{0-2}$ alkyl, aryl, $C_{1-5}$ alkoxy, $C_{1-5}$ alkylthio, amino, $C_{1-5}$ alkylamino, $C_{1-5}$ dialkylamino, $C_{1-5}$ acyl, $C_{1-5}$ alkoxycarbonyl, $C_{1-5}$ acyloxy, $C_{1-5}$ acylamino, $C_{1-5}$ sulphonylamino, hydroxy, halogen, trifluoromethyl, nitro, nitrile, or $R^b$ is chosen from heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl; and $R^7$ is hydrogen.

In another embodiment, there are provided compounds of the formula (I) as described immediately above and wherein Y is —O—, —S—, —NH—, —N(CH$_2$CH$_3$)— or —N(CH$_3$)—;

X is —N(R$^a$)— or —O—;

Q is CH;

each $R^3$, $R^4$ and $R^5$ are hydrogen;

$R^b$ is chosen from hydrogen, $C_{1-5}$ alkyl, $C_{2-5}$ alkenyl, $C_{2-5}$ alkynyl, $C_{3-8}$ cycloalkylC$_{0-2}$ alkyl, aryl, $C_{1-5}$ alkoxy, $C_{1-5}$ alkylthio, amino, $C_{1-5}$ alkylamino, $C_{1-5}$ dialkylamino, $C_{1-5}$ acyl, $C_{1-5}$ alkoxycarbonyl, $C_{1-5}$ acyloxy, $C_{1-5}$ acylamino, $C_{1-5}$ sulphonylamino, hydroxy, halogen, trifluoromethyl, nitro, nitrile or $R^b$ is chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

In yet another embodiment, there are provided compounds of the formula (I) as described immediately above and wherein Y is —O—, —S— or —N(CH$_3$)—;

$R^6$ is present, and is chosen from a bond, —O—, —O—(CH$_2$)$_{1-5}$—, —NH—, —C(O)—NH—, $C_{1-5}$ alkyl branched or unbranched, $C_{2-5}$ alkenyl, $C_{1-3}$ alkyl(OH), heterocycle selected from morpholinyl, piperazinyl, piperidinyl, pyrrolidinyl and tetrahydrofuranyl, or aryl chosen from phenyl and naphthyl, each alkyl, alkenyl, heterocycle and aryl are optionally substituted by one to three hydroxy, $C_{1-3}$ alkyl, $C_{1-3}$ alkoxy, mono or di$C_{1-3}$ alkyl amino, amino or $C_{1-5}$ alkoxycarbonyl;

wherein each $R^6$ is further optionally covalently attached to groups chosen from:

hydrogen, NR$^7$R$^8$, $C_{1-3}$ alkyl, $C_{3-6}$ cycloalkylC$_{0-2}$alkyl, hydroxy, $C_{1-3}$ alkoxy, phenoxy, benzyloxy, phenylC$_{0-4}$ alkyl, piperazinylC$_{0-4}$ alkyl, piperidinyl C$_{0-4}$alkyl, pyrrolidinylC$_{0-4}$ alkyl, morpholinylC$_{0-4}$ alkyl, tetrahydrofuranylC$_{0-4}$ alkyl, triazolyl C$_{0-4}$alkyl, imidazolyl C$_{0-4}$alkyl and pyridinyl C$_{0-4}$alkyl, each above listed heterocycle, heteroaryl and phenyl group is optionally substituted by one to three hydroxy, oxo, $C_{1-4}$ alkyl, $C_{1-3}$ alkoxy, $C_{1-5}$ alkoxycarbonyl, —NR$^7$R$^8$, NR$^7$R$^8$—C(O)— or $C_{1-4}$ acyl;

each R$^7$ and R$^8$ are independently hydrogen, phenylC$_{0-3}$alkyl optionally substituted by halogen, $C_{1-3}$ alkyl or diC$_{1-5}$ alkyl amino, or R$^7$ and R$^8$ are $C_{1-2}$ acyl, benzoyl or $C_{1-5}$ branched or unbranched alkyl optionally substituted by $C_{1-4}$ alkoxy, hydroxy or mono or diC$_{1-3}$ alkyl amino.

In yet another embodiment, there are provided compounds of the formula (I) as described immediately above and wherein X is —O—;
Y is —N(CH$_3$)—;
R$^6$ is chosen from a bond, —O—, —O—(CH$_2$)$_{1-5}$—, —NH—, —C(O)—NH—, $C_{1-5}$ alkyl branched or unbranched, $C_{2-5}$ alkenyl, $C_{1-3}$ alkyl(OH), heterocycle selected from morpholinyl, piperazinyl, piperidinyl and pyrrolidinyl or phenyl, each alkyl, alkenyl, heterocycle and phenyl are optionally substituted by one to three hydroxy, $C_{1-3}$ alkyl, $C_{1-3}$ alkoxy, mono or diC$_{1-3}$ alkyl amino, amino or $C_{1-5}$ alkoxycarbonyl;

wherein each R$^6$ is further optionally covalently attached to groups chosen from:

hydrogen, —NR$^7$R$^8$, $C_{1-3}$ alkyl, $C_{3-6}$ cycloalkylC$_{0-2}$alkyl, benzyloxy, phenylC$_{0-4}$ alkyl, piperazinylC$_{0-4}$ alkyl, piperidinyl $C_{0-4}$alkyl, pyrrolidinylC$_{0-4}$ alkyl, morpholinylC$_{0-4}$ alkyl, triazolyl $C_{0-4}$alkyl, imidazolyl $C_{0-4}$alkyl and pyridinyl C$_{0-4}$alkyl, each above-listed heterocycle, heteroaryl and phenyl group is optionally substituted by one to three hydroxy, oxo, $C_{1-4}$ alkyl, $C_{1-3}$ alkoxy, $C_{1-5}$ alkoxycarbonyl, amino, NR$^7$R$^8$—C(O)— or $C_{1-4}$ acyl;

each R$^7$ and R$^8$ are independently hydrogen, phenylC$_{0-2}$alkyl optionally substituted by halogen, $C_{1-3}$ alkyl or diC$_{1-5}$ alkyl amino, or R$^7$ and R$^8$ are $C_{1-5}$ branched or unbranched alkyl optionally substituted by $C_{1-4}$ alkoxy, hydroxy or mono or diC$_{1-3}$ alkyl amino;

R$^b$ is chosen from hydrogen, $C_{1-5}$ alkyl, $C_{3-7}$ cycloalkylC$_{0-2}$ alkyl, aryl, $C_{1-5}$ alkoxy, amino, $C_{1-5}$ alkylamino, $C_{1-3}$ dialkylamino, $C_{1-3}$ acyl, $C_{1-5}$ alkoxycarbonyl, $C_{1-3}$ acyloxy, $C_{1-3}$ acylamino, $C_{1-3}$ sulphonylamino, hydroxy, halogen, trifluoromethyl, nitro, nitrile;

or R$^b$ is chosen from pyrrolidinyl, pyrrolinyl, morpholinyl, thiomorpholinyl, thiomorpholinyl sulfoxide, thiomorpholinyl sulfone, piperidinyl, piperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl.

In yet still another embodiment, there are provided compounds of the formula (I) as described immediately above and wherein R$^6$ is chosen from a bond, —O—, —O—(CH$_2$)$_{1-5}$—, —NH—, —C(O)—NH—, $C_{1-5}$ alkyl branched or unbranched, $C_{2-5}$ alkenyl, $C_{1-3}$ alkyl(OH), heterocycle selected from morpholinyl, piperazinyl, piperidinyl and pyrrolidinyl or phenyl, each alkyl, alkenyl, heterocycle and phenyl are optionally substituted by one to three hydroxy, $C_{1-3}$ alkyl, $C_{1-3}$ alkoxy, mono or diC$_{1-3}$ alkyl amino, amino or $C_{1-5}$ alkoxycarbonyl;

wherein each R$^6$ is further optionally covalently attached to groups chosen from:

hydrogen, —NR$^7$R$^8$, $C_{1-3}$ alkyl, $C_{3-6}$ cycloalkylC$_{0-2}$alkyl, benzyloxy, phenylC$_{0-4}$ alkyl, piperazinyl, piperazinylC$_{1-2}$ alkyl, piperidinyl, piperidinyl C$_{1-2}$alkyl, pyrrolidinyl, pyrrolidinyl C$_{1-2}$ alkyl, morpholinyl, morpholinylC$_{1-2}$ alkyl, triazolyl, triazolyl C$_{1-2}$alkyl, imidazolyl, imidazolyl C$_{1-2}$alkyl, pyridinyl and pyridinyl C$_{1-2}$alkyl, each above-listed heterocycle, heteroaryl and phenyl group is optionally substituted by one to three hydroxy, oxo, $C_{1-4}$ alkyl, $C_{1-3}$ alkoxy, $C_{1-5}$ alkoxycarbonyl, amino, NR$^7$R$^8$—C(O)— or $C_{1-4}$ acyl.

In yet another embodiment, there are provided compounds of the formula (I) as described immediately above and wherein R$^b$ is chosen from hydrogen, $C_{1-5}$ alkyl, $C^{3-6}$ cycloalkylC$_{0-2}$ alkyl, phenyl, $C_{1-5}$ alkoxy, amino, $C_{1-5}$ alkylamino, $C_{1-3}$ dialkylamino, $C_{1-3}$ acyl, $C_{1-5}$ alkoxycarbonyl, $C_{1-3}$ acyloxy, $C_{1-3}$ acylamino, hydroxy, halogen;

or R$^b$ is chosen from morpholinyl, thiomorpholinyl, thiomorpholinyl sulfoxide, thiomorpholinyl sulfone, piperidinyl, piperidinonyl, pyridinyl, pyrimidinyl, pyrazinyl and pyridazinyl.

In yet another embodiment, there are provided compounds of the formula (I) as described immediately above and wherein R$^b$ is chosen from amino, $C_{1-5}$ alkylamino, $C_{1-3}$ dialkylamino;
or R$^b$ is chosen morpholinyl, piperidinyl and pyridinyl.

In yet another embodiment, there are provided compounds of the formula (I) as described immediately above and wherein Rx is chosen from:

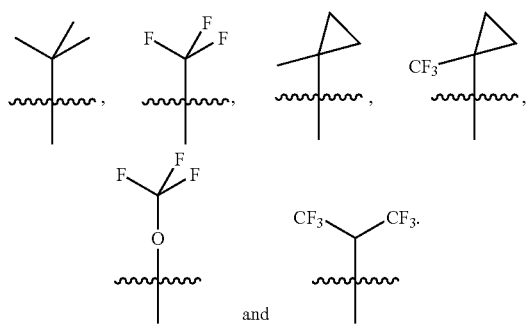

For any of the above described embodiments, preferred embodiments where Ar1 is (i) and includes:

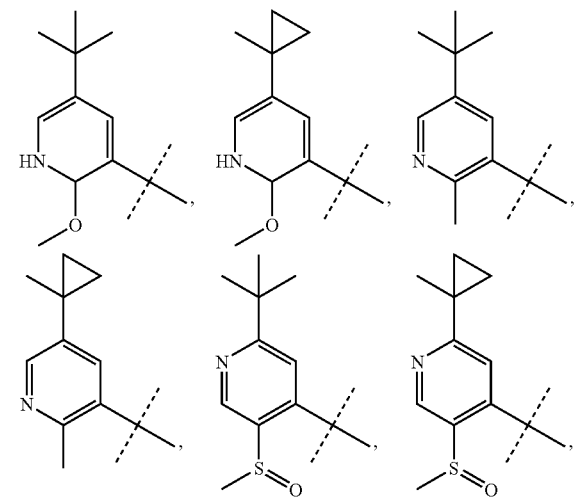

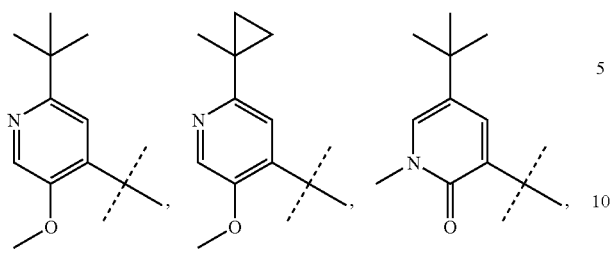
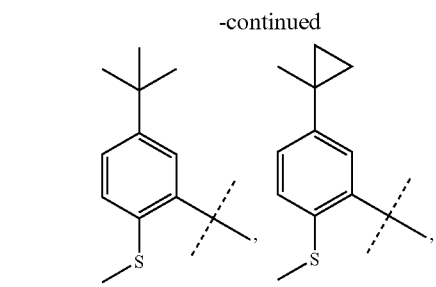
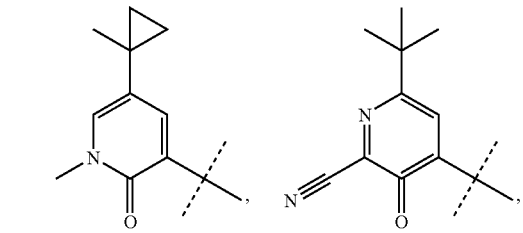
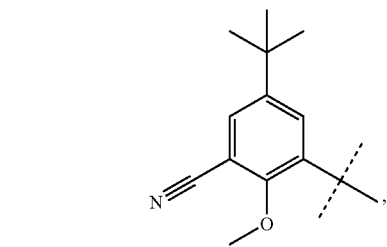
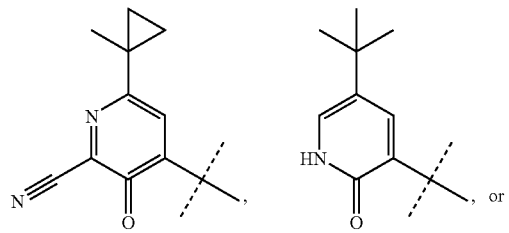
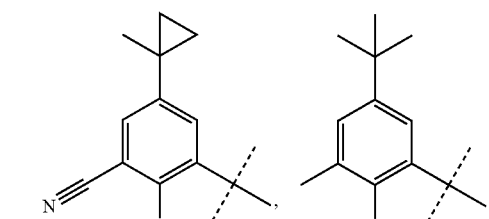
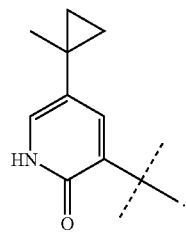
For any of the above described embodiments, preferred embodiments where Ar¹ is (ii) include:
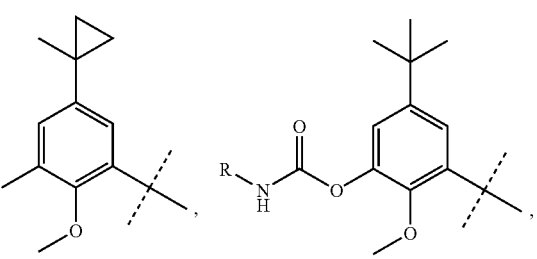
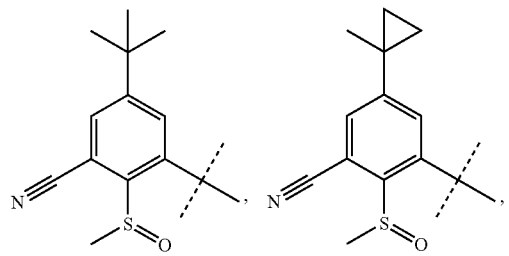
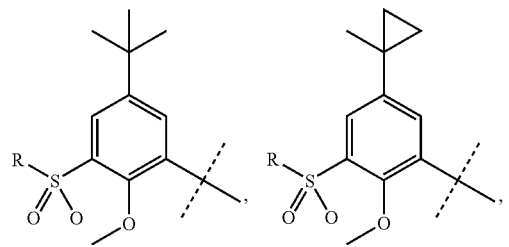
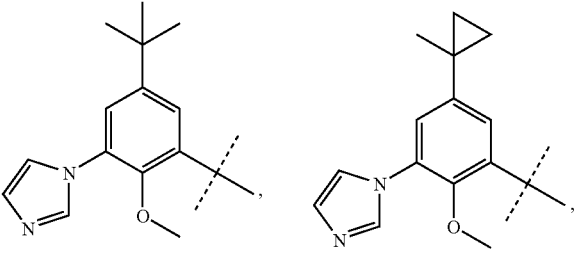

-continued
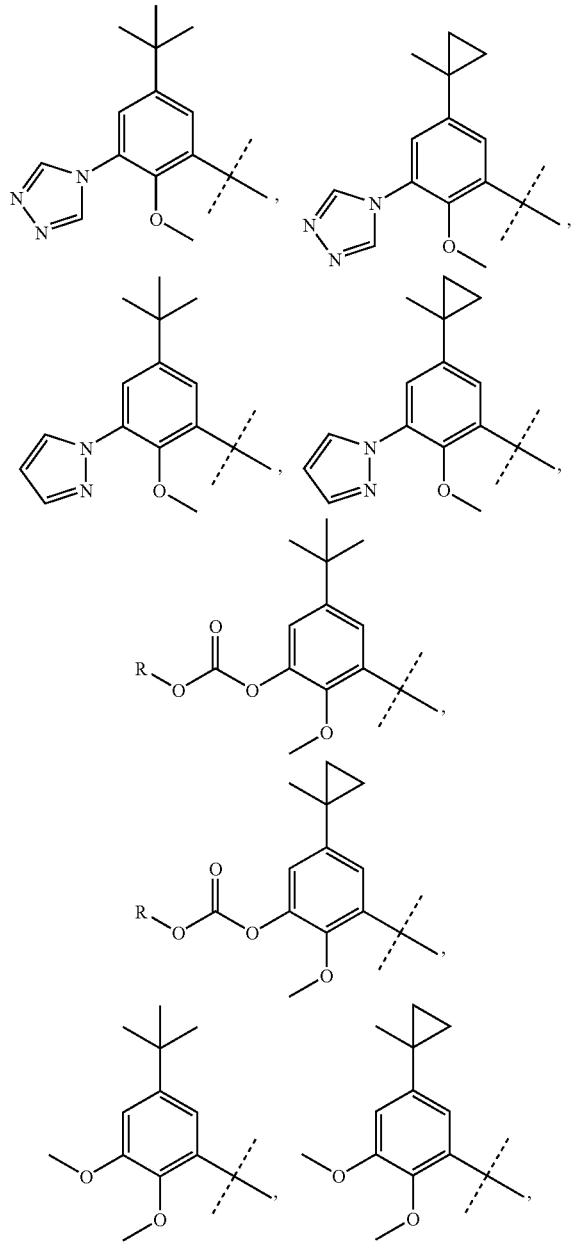
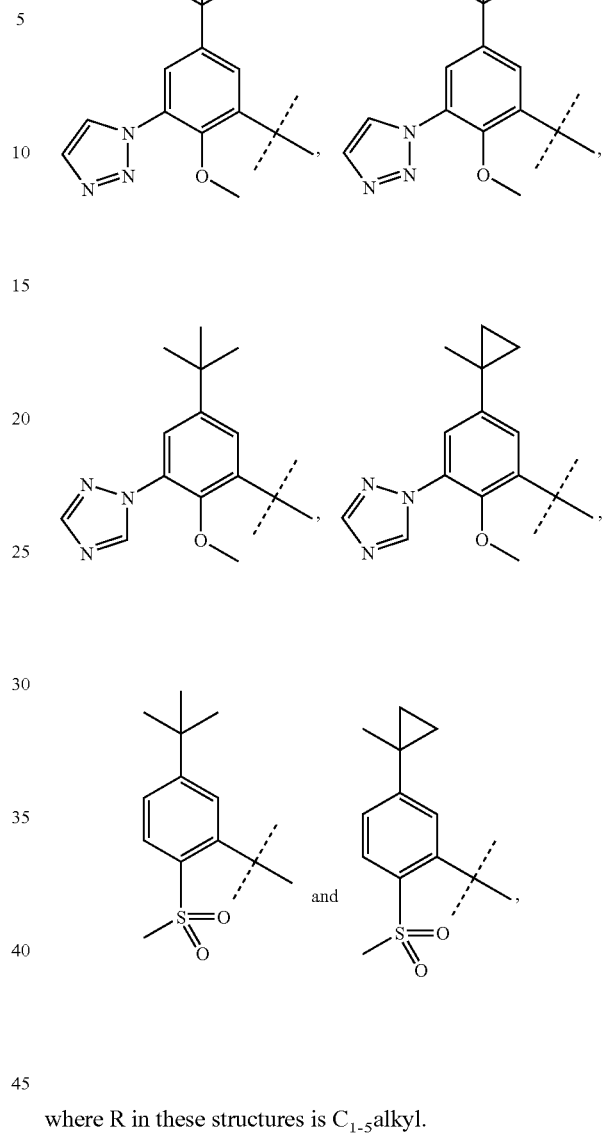
where R in these structures is $C_{1-5}$alkyl.
The following are representative compounds of the invention:
TABLE I
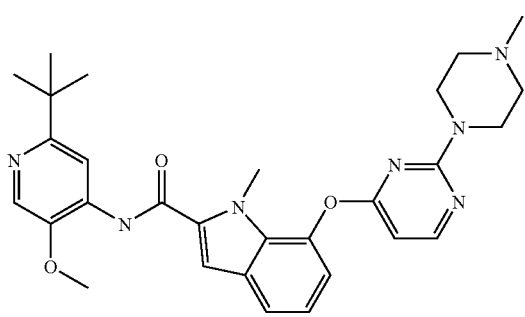
1-Methyl-7-[2-(4-methyl-piperazin-1-yl)-pyrimidin-4-yloxy]-1H-indole-2-carboxylic acid (2-tert-butyl-5-methoxy-pyridin-4-yl)-amide TABLE I-continued

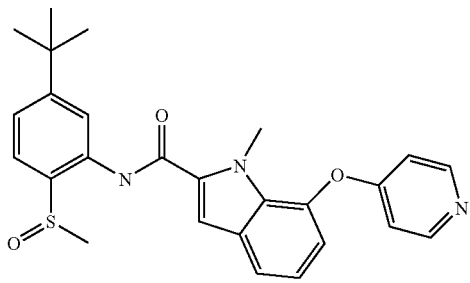

1-Methyl-7-(pyridin-4-yloxy)-1H-indole-2-carboxylic acid (5-tert-butyl-2-methanesulfinyl-phenyl)-amide

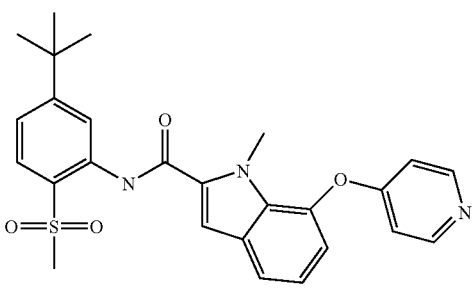

1-Methyl-7-(pyridin-4-yloxy)-1H-indole-2-carboxylic acid (5-tert-butyl-2-methanesulfonyl-phenyl)-amide

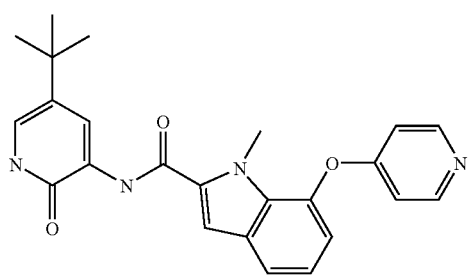

1-Methyl-7-(pyridin-4-yloxy)-1H-indole-2-carboxylic acid (5-tert-butyl-2-oxo-1,2-dihydro-pyridin-3-yl)-amide

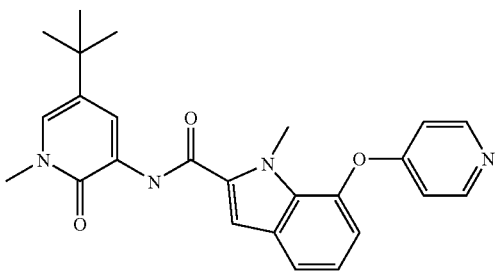

1-Methyl-7-(pyridin-4-yloxy)-1H-indole-2-carboxylic acid (5-tert-butyl-1-methyl-2-oxo-1,2-dihydro-pyridin-3-yl)-amide

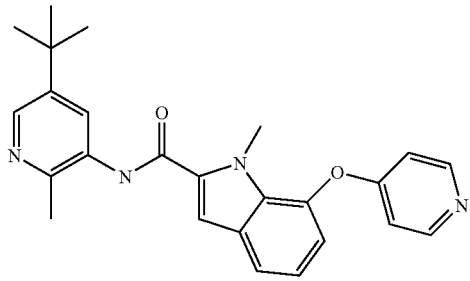

1-Methyl-7-(pyridin-4-yloxy)-1H-indole-2-carboxylic acid (5-tert-butyl-2-methyl-pyridin-3-yl)-amide TABLE I-continued

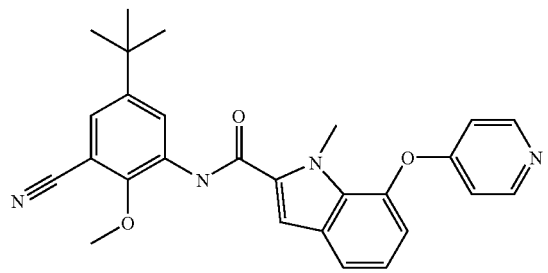

1-Methyl-7-(pyridin-4-yloxy)-1H-indole-2-carboxylic acid (5-tert-butyl-3-cyano-2-methoxy-phenyl)-amide

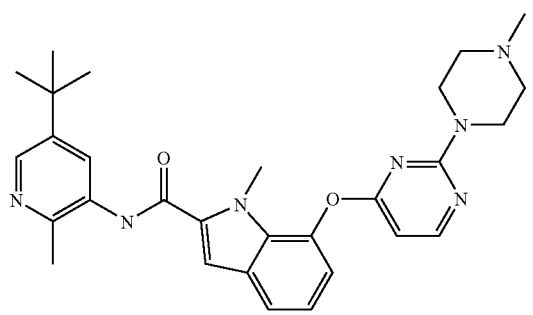

1-Methyl-7-[2-(4-methyl-piperazin-1-yl)-pyrimidin-4-yloxy]-1H-indole-2-carboxylic acid (5-tert-butyl-2-methyl-pyridin-3-yl)-amide

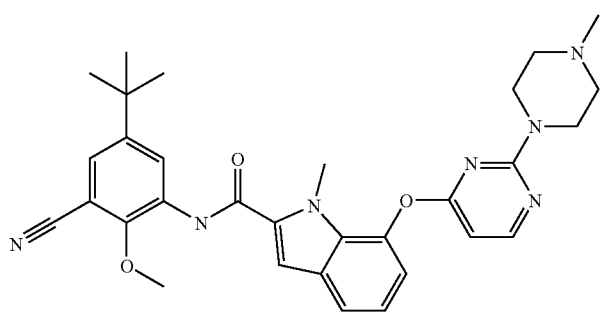

1-Methyl-7-[2-(4-methyl-piperazin-1-yl)-pyrimidin-4-yloxy]-1H-indole-2-carboxylic acid (5-tert-butyl-3-cyano-2-methoxy-phenyl)-amide

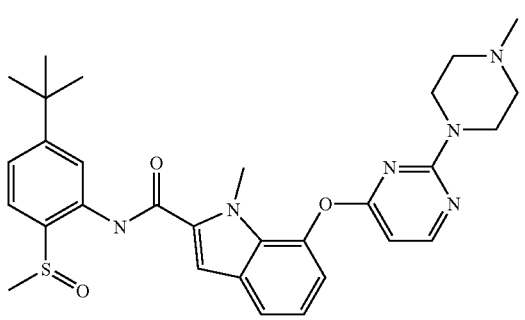

1-Methyl-7-[2-(4-methyl-piperazin-1-yl)-pyrimidin-4-yloxy]-1H-indole-2-carboxylic acid (5-tert-butyl-2-methanesulfinyl-phenyl)-amide

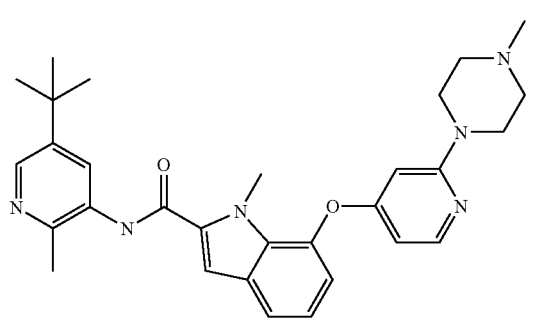

1-Methyl-7-[2-(4-methyl-piperazin-1-yl)-pyridin-4-yloxy]-1H-indole-2-carboxylic acid (5-tert-butyl-2-methyl-pyridin-3-yl)-amide TABLE I-continued

| Structure | Name |
|---|---|
| 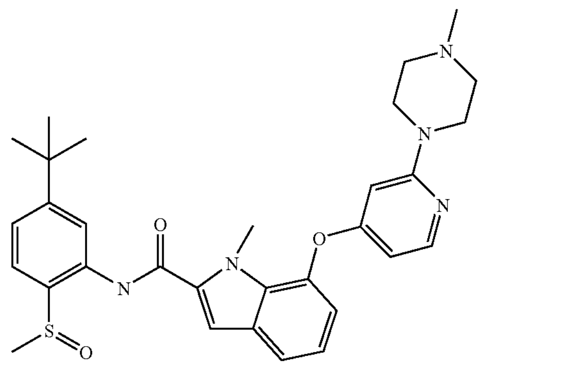 | 1-Methyl-7-[2-(4-methyl-piperazin-1-yl)-pyridin-4-yloxy]-1H-indole-2-carboxylic acid (5-tert-butyl-2-methanesulfinyl-phenyl)-amide |
| 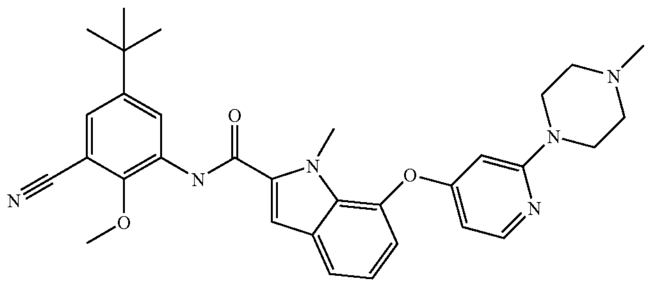 | 1-Methyl-7-[2-(4-methyl-piperazin-1-yl)-pyridin-4-yloxy]-1H-indole-2-carboxylic acid (5-tert-butyl-3-cyano-2-methoxy-phenyl)-amide |
| 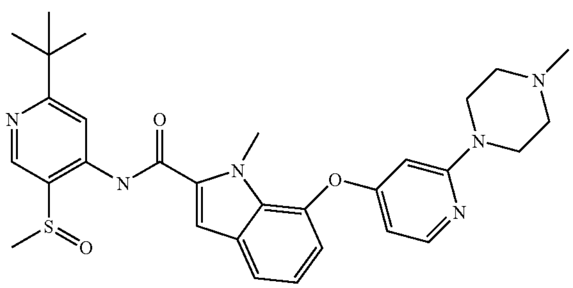 | 1-Methyl-7-[2-(4-methyl-piperazin-1-yl)-pyridin-4-yloxy]-1H-indole-2-carboxylic acid (2-tert-butyl-5-methanesulfinyl-pyridin-4-yl)-amide |
| 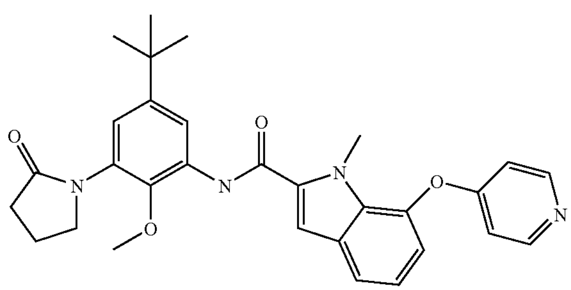 | 1-Methyl-7-(pyridin-4-yloxy)-1H-indole-2-carboxylic acid [5-tert-butyl-2-methoxy-3-(2-oxo-pyrrolidin-1-yl)-phenyl]-amide |
| 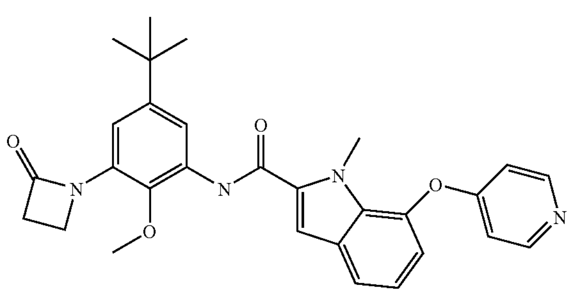 | 1-Methyl-7-(pyridin-4-yloxy)-1H-indole-2-carboxylic acid [5-tert-butyl-2-methoxy-3-(2-oxo-azetidin-1-yl)-phenyl]-amide |

TABLE I-continued

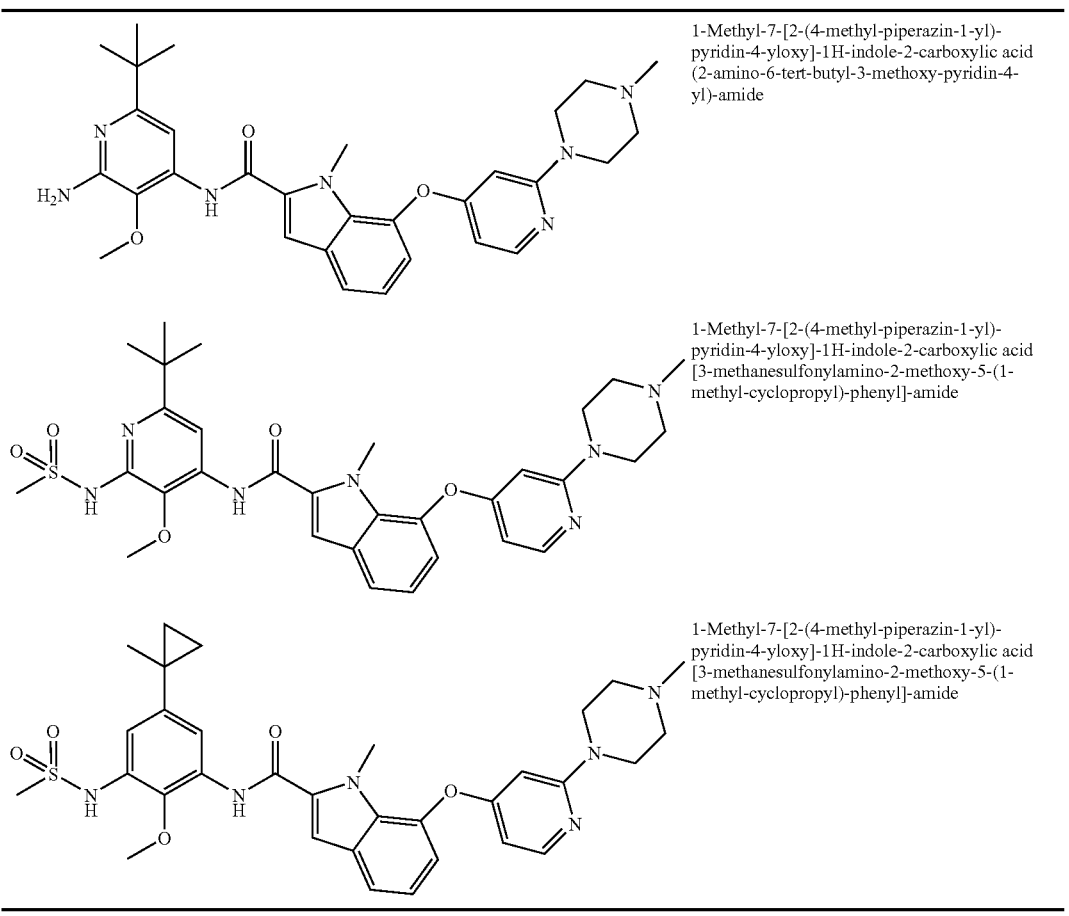

| Structure | Name |
|---|---|
| (top) | 1-Methyl-7-[2-(4-methyl-piperazin-1-yl)-pyridin-4-yloxy]-1H-indole-2-carboxylic acid (2-amino-6-tert-butyl-3-methoxy-pyridin-4-yl)-amide |
| (middle) | 1-Methyl-7-[2-(4-methyl-piperazin-1-yl)-pyridin-4-yloxy]-1H-indole-2-carboxylic acid [3-methanesulfonylamino-2-methoxy-5-(1-methyl-cyclopropyl)-phenyl]-amide |
| (bottom) | 1-Methyl-7-[2-(4-methyl-piperazin-1-yl)-pyridin-4-yloxy]-1H-indole-2-carboxylic acid [3-methanesulfonylamino-2-methoxy-5-(1-methyl-cyclopropyl)-phenyl]-amide | or the pharmaceutically acceptable salts and/or isomers thereof.

In all the compounds disclosed hereinabove in this application, in the event the nomenclature is in conflict with the structure, it shall be understood that the compound is defined by the structure.

Of particular importance according to the invention are compounds of formula (I), for use as pharmaceutical compositions with an anti-cytokine activity.

The invention also relates to the use of a compound of formula (I), for preparing a pharmaceutical composition for the treatment and/or prevention of a cytokine mediated disease or condition.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N,O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The invention additionally provides for methods of making the compounds of the formula (I). The compounds of the invention may be prepared by the general methods and examples presented below, and methods known to those of ordinary skill in the art. Further reference in this regard may be made to U.S. Pat. No. 6,358,945, U.S. application Ser. Nos. 09/714,539, 09/834,797, 10/120,028, 10/143,322 and 10/147,675. U.S. application Ser. No. 10/264,689 teaches additional methods for preparation of sulfonamide intermediates. Each of the aforementioned U.S. cases are incorporated in their entirety.

In all schemes, unless otherwise specified, $Ar^1$, X, Y, W and $R^3$-$R^6$ in the formulas shown below shall have the meanings defined for these groups in the definition of the formula (I) of the invention, described hereinabove. Intermediates used in the syntheses below are either commercially available or easily prepared by methods known to those skilled in the art. Reaction progress may be monitored by conventional methods such as thin layer chromatography (TLC). Intermediates and products may be purified by methods known in the art, including column chromatography, HPLC or recrystallization.

Compounds of the invention where Q is a carbon atom, may be prepared as described in Schemes I and II. Compounds of the invention wherein Q is a nitrogen atom, may be prepared by analogous methods which will be apparent to one of ordinary skill in the art.

such as palladium on carbon in a suitable solvent such as EtOH. The resulting intermediate V may then be coupled with the desired halo heterocycle VI (Z=halogen) bearing $R^6$ in the presence of a suitable base to provide I. $Ar^1$ and $R^6$ may be further modified by standard synthetic methods known in the art to produce additional compounds of formula (I). Several examples are described in the Synthetic Examples section below.

In a modification of the above method, the order of coupling VI and $Ar^1NH_2$ with the central heterocycle may be reversed. This is illustrated in Scheme II.

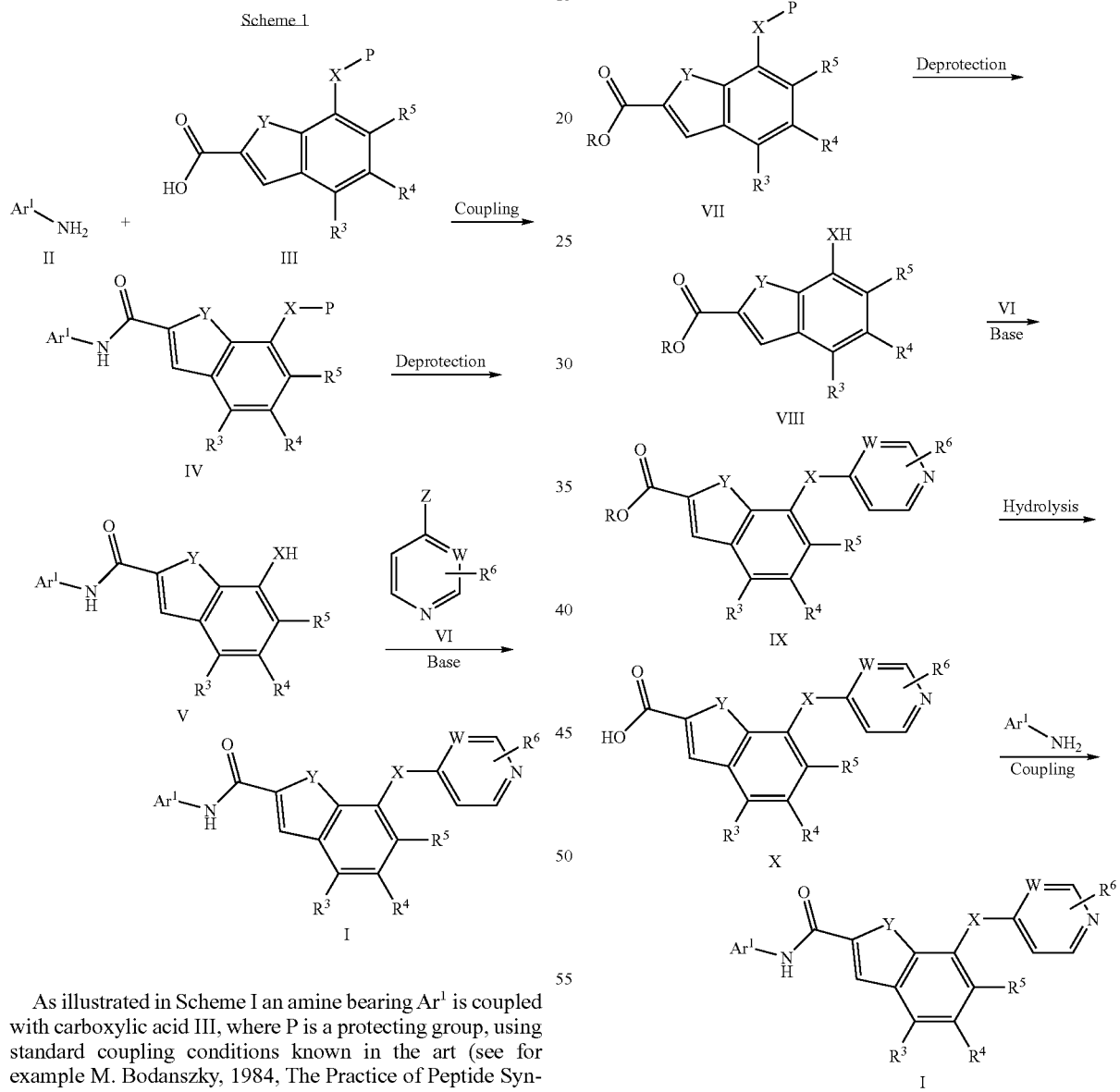

As illustrated in Scheme I an amine bearing $Ar^1$ is coupled with carboxylic acid III, where P is a protecting group, using standard coupling conditions known in the art (see for example M. Bodanszky, 1984, The Practice of Peptide Synthesis, Springer-Verlag). For example, one may couple III and II by treating with 1-[3-(dimethylamino)propyl]-3-ethylcarbodiimide hydrochloride (EDC) followed by 1-hydroxybenzotriazole hydrate (HOBT) in a suitable solvent such as DMF. Removal of the protecting group P to provide V may be achieved by standard procedures known in the art. For example, if P is a benzyl group, it may be removed by treatment of IV with hydrogen gas in the presence of a catalyst As illustrated above, the ester VII (R=lower alkyl such as methyl or ethyl, P=a protecting group) is deprotected as described above and the resulting intermediate VIII is coupled, as described above to provide ester IX. This is hydrolyzed using standard hydrolysis conditions and the resulting acid coupled with $Ar^1NH_2$ to provide I. As above, Ar[1] and R[6] may be further modified by standard synthetic methods known in the art to produce additional compounds of formula (I). Several examples are described in the Synthetic Examples section below.

SYNTHETIC EXAMPLES

Example 1

1-Methyl-7-[2-(4-methyl-piperazin-1-yl)-pyridin-4-yloxy]-1H-indole-2-carboxylic acid (5-tert-butyl-3-methanesulfonylamino-2-methoxy-phenyl)-amide For a similar procedure to form the indole core, see R. Albrecht et al. *Eur. J. Med. Chem. Chim. Ther.* 1985, 20, 59-60.

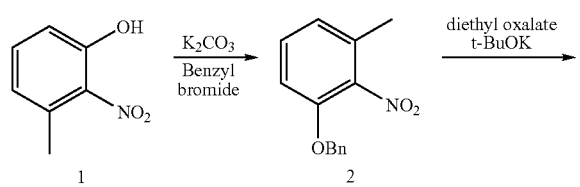

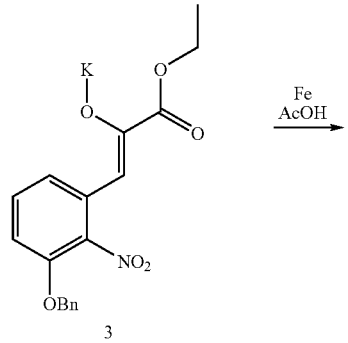

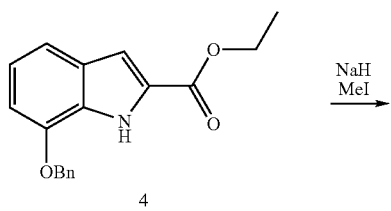

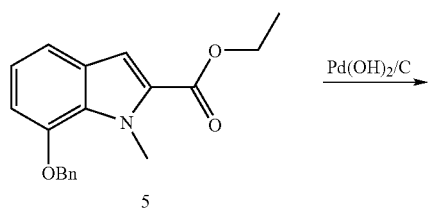

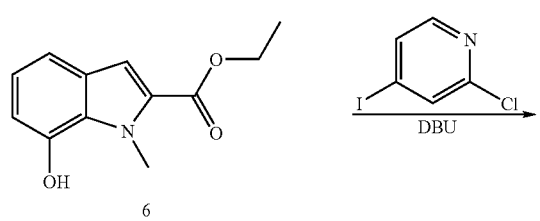

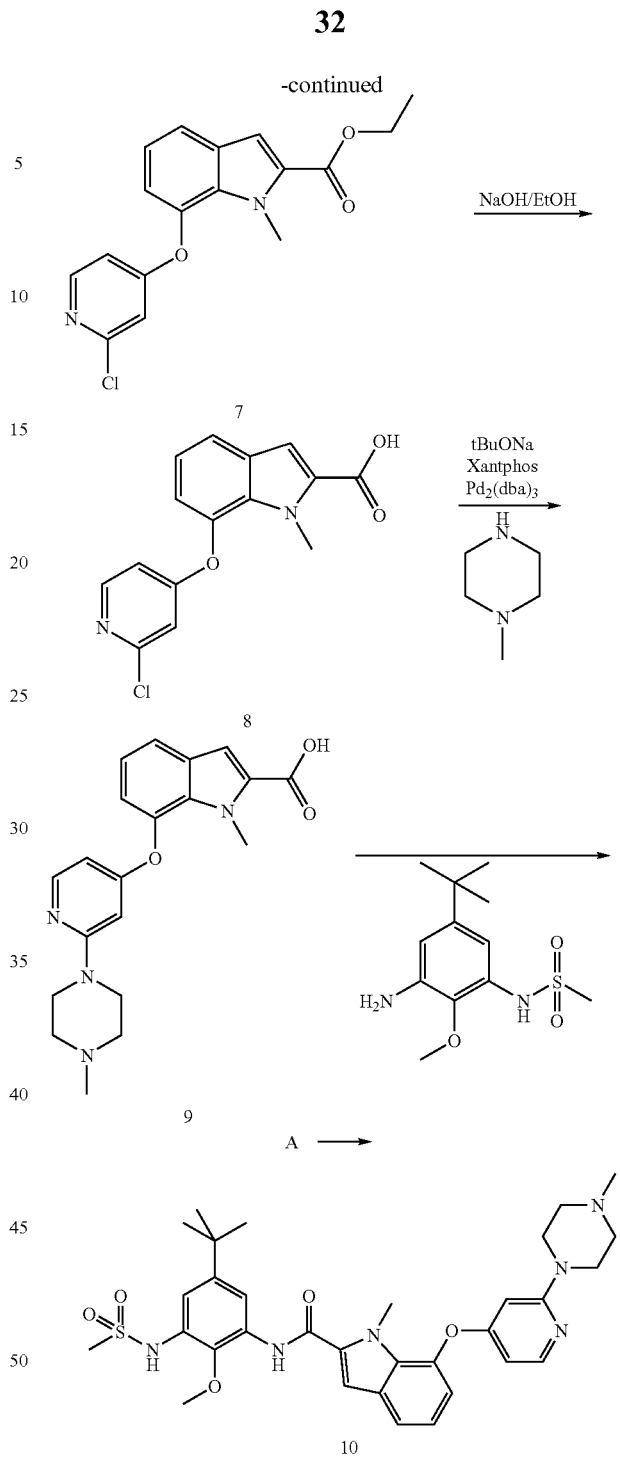

Preparation of 1-Benzyloxy-3-methyl-2-nitro-benzene (Compound 2)

To a mechanically stirred solution of 1 (760 g, 4.96 mol) in acetonitrile (12.1 L) was added potassium carbonate (857 g, 6.2 mol). Benzyl bromide (590 mL, 4.96 mol) was added to the dark red suspension over 5 h which raised the temperature slightly. The reaction was heated to 75° C. over 45 min and then held at 75° C. for 2 h over which time the reaction turned orange. The reaction was allowed to cool to 40° C. and water (6.2 L) was added. The reaction was transferred to a separatory funnel and the reaction flask washed with ethyl acetate (1 L) to complete the transfer. The layers were separated and the aqueous layer extracted with ethyl acetate (6 L). The combined organics were washed with brine (5 L) and then dried over sodium sulfate. The mixture was filtered through celite and concentrated to an orange oil. The oil was redissolved in ethyl acetate and filtered through celite a second time to remove residual solids. The solution was then concentrated and dried under vacuum to give 2 (1199 g, 99%) as an orange oil.

Preparation of 3-(3-Benzyloxy-2-nitro-phenyl)-2-hydroxy-acrylic acid ethyl ester potassium salt (Compound 3)

To a stirred solution of MTBE (16 L) was added a 1 M solution of potassium t-butoxide in THF (4.9 L, 4.9 mol). Diethyl oxalate (667 mL, 4.9 mol) was added via addition funnel causing a slight exotherm. A solution of 2 (1199 g, 4.9 mol) in MTBE (2 L) was added over 1 h. The reaction was stirred at room temperature for 3 h and then heated at reflux overnight. The reaction was allowed to cool to room temperature and the solids were collected by vacuum filtration, washed with MTBE, and dried under vacuum to give compound 3 as an orange solid (1398 g, 74%).

Preparation of 7-Benzyloxy-1H-indole-2-carboxylic acid ethyl ester (Compound 4)

A suspension of iron powder (2783 g, 50 mol) in acetic acid (12.3 L) was heated to 50° C. A solution of 3 (1422 g, 3.72 mol) in acetic acid (4.2 L) was added over 3.5 h in an exothermic reaction. The reaction was heated at 80° C. for 12 h. The reaction was cooled to 50° C. and ethyl acetate (16 L) was added and the suspension stirred for 0.5 h. The suspension was filtered through celite and washed through with ethyl acetate (8 L). The filtrate was concentrated to a brown paste. The paste was redissolved in ethyl acetate (16 L) and a 0.4 M solution of tetrasodium EDTA (16 L) was added. The solution was saturated with solid sodium bicarbonate and stirred overnight. The layers were separated and the aqueous layer extracted with ethyl acetate (4 L). The combined organics were washed with saturated sodium bicarbonate (2×7 L) and then washed with a 0.4 M solution of tetrasodium EDTA (7 L). The organics were dried over sodium sulfate for 5 h and then filtered through a pad of silica gel washing through with ethyl acetate. The filtrate was concentrated to give compound 4 (905 g, 82%) as a dark brown solid.

Preparation of 7-Benzyloxy-1-methyl-1H-indole-2-carboxylic acid ethyl ester (Compound 5)

A suspension of sodium hydride (132 g, 3.43 mol, 60% dispersion in mineral oil) was cooled to 10° C. in an ice bath. A solution of 4 (844 g, 2.86 mol) in DMF (1.9 L) was added over 4.5 h with a slight exotherm raising the temperature to 13° C. The reaction was stirred for an additional 0.5 h. Methyl iodide (180 mL, 2.86 mol) was added over 1 h raising the temperature from 12.6° C. to 18.8° C. The reaction was stirred overnight under nitrogen. The reaction was quenched with saturated ammonium chloride (700 mL) causing a tan precipitate and an exotherm. Water (3 L) was added and the solids were collected by vacuum filtration and washed with water (2 L). The solids (~1.5 kg) were dissolved in ethyl acetate (4 L) and washed with brine (1 L). The ethyl acetate solution was treated with sodium sulfate and charcoal for 1 h. The mixture was filtered through celite and concentrated to a brown solid. The solid (964 g) was mostly dissolved in 2% ethyl acetate in hepatane (4.8 L), decanted from the oily residue, and the solution was filtered and concentrated a dark yellow solid. The oily residue was dissolved in ethyl acetate (5 volumes) and diluted with heptane (5 volumes based on ethyl acetate) and the resulting precipitate collected by vacuum filtration. The solids were combined and slurried with heptane (3 volumes), filtered, and dried under vacuum for 2 days to give compound 5 (686 g, 76%) as a tan powder: mp 59-61° C.

Preparation of 7
7-Hydroxy-1-methyl-1H-indole-2-carboxylic acid ethyl ester (Compound 6)

5 (82.2 g, 266 mmol) and Pearlman's catalyst (2.0 g; 20% Pd(OH)$_2$/C, wet, Aldrich) were suspended in EtOH (300 mL) in a Parr Shaker jar. The jar was purged with H$_2$ and shaken at RT (Parr shaker) under a constant 10 psi of H$_2$ for 5 h. The final solution was filtered through Celite 545 and concentrated to give the product (58.15 g; 99%) as an analytically pure, off-white solid.

Preparation of 7-(2-Chloro-pyridin-4-yloxy)-1-methyl-1H-indole-2-carboxylic acid ethyl ester (Compound 7)

The indole substrate (135.0 g, 602 mmol) and 2-chloro-4-iodopyridine (147 g, 614 mmol) were dissolved in anhydrous DMF (150 mL) under an atmosphere of N$_2$. DBU 144 mL, 963 mmol) was added in one portion. The reaction was stirred at 110° C. for 16 hours, then cooled and concentrated under high vacuum. The dark residue was taken up in EtOAc (1500 ml) and washed successively with 50% brine (300 mL), 5% aqueous citric acid (2×300 mL), saturated aqueous sodium bicarbonate (2×300 mL), and brine (300 ml). The organic layer was dried over MgSO$_4$/decolorizing charcoal, filtered, and concentrated to give a dark red-purple solid. Recrystallization from MeCN (260 mL) gave the product as pale purple crystals (199 g, 67%).

Preparation of 7-(2-Chloro-pyridin-4-yloxy)-1-methyl-1H-indole-2-carboxylic acid (Compound 8)

The ester (53.2 g, 161 mmol) was dissolved in 1:1 THF/EtOH (1000 mL). 1M aqueous NaOH (370 mL, 370 mmol) was added over 30 minutes with vigorous stirring. The solution was stirred at RT for 5 hours. Water (500 mL) was then added, and the bulk of the organic solvents removed by rotary evaporation (60° C.). The resulting aqueous solution was washed with Et$_2$O (2×200 mL) and the organic extracts discarded. The dark aqueous solution was acidified to pH 5.2 (pH meter) with 10% HCl and then extracted with EtOAc (4×400 mL). The combined organic extracts were washed with brine (300 mL), dried over MgSO$_4$, filtered, and concentrated. The residue was dissolved in the minimum amount of hot acetonitrile and decolorizing carbon added. The solution was refluxed for 5 minutes, and then filtered through a pad of Celite which was subsequently washed with hot acetonitrile (2×100 mL). The product crystallized on cooling and was collected by filtration giving the desired acid as an off-white, analytically pure solid (46 g, 95%).

Preparation of 1-Methyl-7-[2-(4-methyl-piperazin-1-yl)-pyridin-4-yloxy]-1H-indole-2-carboxylic acid (Compound 9)

Flush with $N_2$ a 3-neck 250 mL round bottom flask equipped with an overhead stirrer, reflux condensor, thermocouple thermometer, heating mantle and $N_2$ line. Charge 8 (6 g, 19 mmol) into the flask followed by t-BuONa (69 mmol) and toluene (99 mL). Charge piperazine (39.6 mmol) into the flask. A mild exotherm brings the internal temperature to 30° C. Purge the solution by sparging with $N_2$ 5-10 min. Charge Xantphos (69 mmol) followed by Pd (0.3 mmol). Purge the mixture again by sparging with $N_2$ for 5-10 min. Heat the mixture to 95-100° C. and stir under $N_2$ for 4 h. Cool the mixture to 22-25° C. and add water (60 mL). Stir for 2-5 min and set aside the aqueous portion. Extract the organic portion with 0.3 M NaOH (35 mL). The combined aqueous portions were filtered through a pad of Darco G-60 charcoal and celite. The pad was filtered with 2 mL 0.3 M NaOH. Place the combined aqueous portions over a bath at 20-25° C. and neutralize the solution to pH=6-7 with 2N HCl. The solution is stirred for 20 min to 30 min the solid by is collected by filtration. The cake is rinsed with MTBE (20 mL) and air-dried overnight. The solid is dried by azeotropic distillation of a slurry with THF (3×75 mL) and then in a vacuum oven at 50° C. for a minimum of 6 h to afford 7.83 g (87%) of an off-white solid.

Preparation of 1-Methyl-7-[2-(4-methyl-piperazin-1-yl)-pyridin-4-yloxy]-1H-indole-2-carboxylic acid (5-tert-butyl-3-methanesulfonylamino-2-methoxy-phenyl)-amide (Compound 10)

Charge 9 (6.0 g, 16.4 mmol) into a flask followed by THF (96.0 mL) and DMF (0.05 mL). Add oxalyl chloride (1.5 mL) slowly keeping the internal temperature at 20-25° C. Stir for approx. 1.5 h. Aniline (18 mmol) and DMAP (catalytic) were added in one portion followed by $Et_3N$ (2.65 mL). The mixture is stirred at ambient temperature for 2 hours.

The mixture was quenched with 5% $NaHCO_3$ (70 mL) and stirred for 10 min. The organic portion was removed and the aqueous was extracted with ethyl acetate (1×70 mL) and MeTHF (1×70 mL). The combined organic portions were washed with 5% NaCl (70 mL), dried ($Na_2SO_4$) and concentrated under reduced pressure to afford a brown oil. The resulting oil was dissolved in acetonitrile (55.0 mL) at 55° C., allowed to reach 25-30° C. and filtered. The cake was rinsed with 5 mL acetonitrile. The mixture was then concentrated to an oil (approx. 30-40% by weight), diluted with acetonitrile at 50° C. The resulting solid was collected by filtration. The cake was washed with acetonitrile (2×12 mL) and air dried for 1 h. The product was dried in a vacuum over at 50° to afford 3.52 g (34.7%) of an off-white solid.

Example 2

Synthesis of 1-methyl-7-[2-(4-methyl-piperazin-1-yl)-pyrimidin-4-yloxy]-1H-indole-2-carboxylic acid (2-tert-butyl-5-methoxy-pyridin-4-yl)-amide

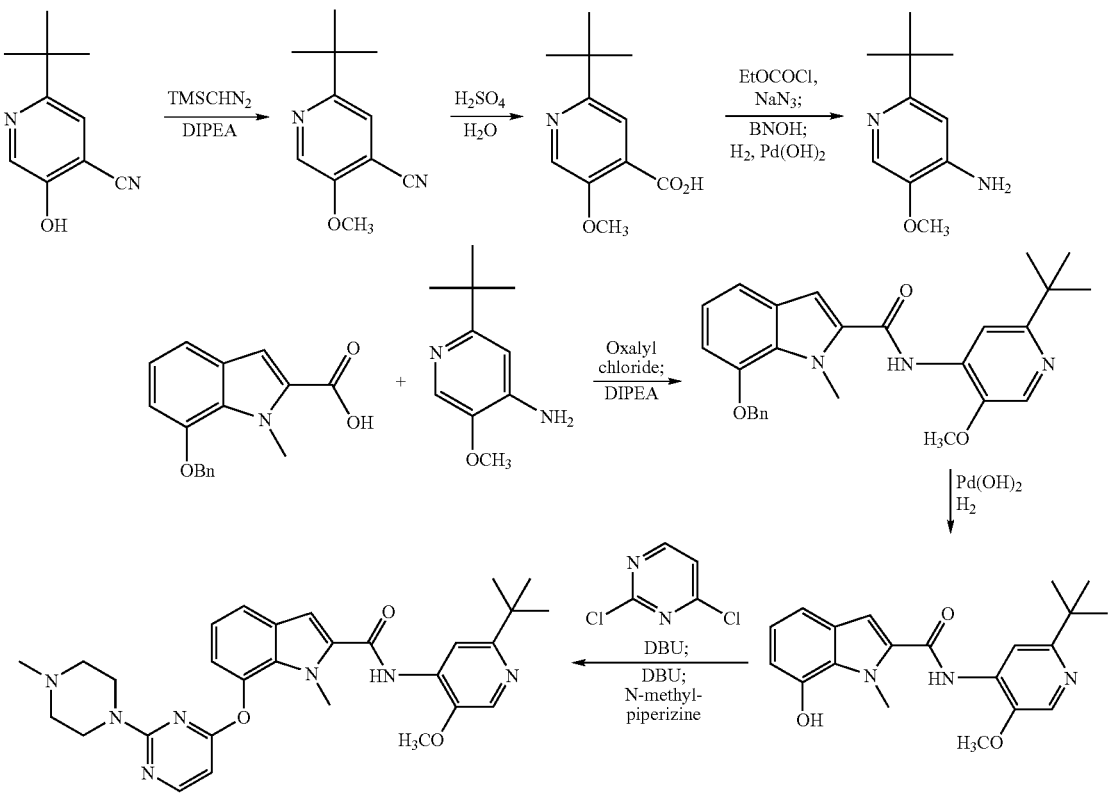

To a solution of 2-tert-butyl-5-hydroxy-isonicotinonitrile (10.0 g, 73.5 mmol) in acetonitrile/methanol (9:1, 20 mL) was added N,N-diisopropylethylamine (1.48 mL, 8.52 mmol) followed by (trimethylsilyl)diazomethane (2.0M in hexane, 4.30 mL, 8.52 mmol). The red solution was stirred for 18 h at room temperature and then concentrated in vacuo. The residue was dissolved in methylene chloride, washed with saturated aqueous NaHCO₃ dried over sodium sulfate, filtered, and concentrated in vacuo to provide 2-tert-butyl-5-methoxy-isonicotinonitrile (1.10 g, 99%) as a pale yellow oil which was utilized without further purification.

The above nitrile (1.10 g, 5.68 mmol) was dissolved in aqueous sulfuric acid (9.0 M in water, 6.0 mL) and heated to 120° C. for 8 h. The solution was cooled to room temperature and NaOH (~2.0 g) was added slowly to neutralize the solution. The mixture was then diluted with an equal volume of saturated aqueous KH₂PO₄ and extracted several times with 25% 2-propanol in chloroform. The extracts were combined, dried over sodium sulfate, filtered, and concentrated in vacuo to provide 2-tert-butyl-5-methoxy-isonicotinic acid (1.09 g, 92%) as a pale brown solid which was utilized without further purification.

Ethyl chloroformate (101 microL, 1.05 mmol) was added dropwise to a solution of the above acid (200 mg, 0.96 mmol) and N,N-diisopropylethylamine (183 microL, 1.05 mmol) in acetone (1.0 mL) at 0° C. The mixture was stirred for 0.5 h at 0° C. then warmed to room temperature and stirred an additional 0.5 h. Lastly, a solution of sodium azide (5.0 M in water, 400 μL, 2.00 mmol) was added and the resultant slurry was stirred at room temperature for 1 h. Water was added to the reaction mixture and the aqueous phase was extracted with methylene chloride. Toluene (2 mL) was added to the combined extracts which were subsequently dried over sodium sulfate, filtered, and concentrated in vacuo to a volume of 1 mL (Caution was taken to avoid complete concentration). The resultant toluene solution of the acyl azide was then added dropwise to a refluxing solution of benzyl alcohol (120 microL, 1.15 mmol) in toluene (1 mL) and the mixture was refluxed an additional 1.5 h. Concentration in vacuo, followed by filtration of the residue through a plug of silica-gel with diethyl ether provided the crude Cbz-protected aniline. This crude product was immediately dissolved in ethanol/water (10:1, 3.0 mL) in a Parr hydrogenation vessel and Pd(OH)₂ (20% on carbon, 20 mg) was added. The reaction was placed under a hydrogen atmosphere (50 psi) and shaken at room temperature for 0.25 h. The solution was then filtered through diatomaceous earth, concentrated and the residue was purified by silica-gel chromatography (ethyl acetate) to provide 2-tert-butyl-5-methoxy-pyridin-4-ylamine (95 mg, 56%) as a white solid.

To a slurry of 7-benzyloxy-1-methyl-1H-indole-2-carboxylic acid (163 mg, 0.58 mmol) in methylene chloride (2 mL) at 0° C. was added oxalyl chloride (72 microL, 0.84 mmol) followed by a drop of N,N-dimethylformamide. The solution immediately bubbled and became clear after a period of 0.75 h. The mixture was concentrated and redissolved in methylene chloride (1.5 mL). The acid chloride solution was added to a solution of N,N-diisopropylethylamine (202 microL, 1.16 mmol) and 2-tert-butyl-5-methoxy-pyridin-4-ylamine (95 mg, 0.52 mmol) in methylene chloride (1.5 mL). The solution was stirred at room temperature for 3 h then poured onto saturated aqueous NaHCO₃. The aqueous layer was extracted with methylene chloride and the combined extracts were washed with saturated aqueous NaHCO₃, followed by saturated aqueous KH₂PO₄, and again with saturated aqueous NaHCO₃. The organic extracts were dried over sodium sulfate, filtered through a plug of silica-gel with diethyl ether, and concentrated in vacuo to provide pure 7-benzyloxy-1-methyl-1H-indole-2-carboxylic acid (2-tert-butyl-5-methoxy-pyridin-4-yl)-amide (231 mg, 99%) as a white solid.

Pd(OH)₂ (20% on C, 24 mg) was added to a solution of the above indole (231 mg, 0.52 mmol) in ethanol/ethyl acetate (3:2, 5.0 mL) at room temperature. The solution was placed under a hydrogen atmosphere (1 atm) and stirred at room temperature for 18 h. The mixture was filtered through diatomaceous earth and concentrated in vacuo to provide 7-hydroxy-1-methyl-1H-indole-2-carboxylic acid (2-tert-butyl-5-methoxy-pyridin-4-yl)-amide (199 mg, 99%) as a pale brown solid.

A solution of the above indole amide (93 mg, 0.26 mmol) and DBU (40 micro L, 0.26 mmol) in acetonitrile (1.0 mL) was added dropwise to a slurry of 2,4-dichloropyrimidine (39 mg, 0.26 mmol) in acetonitrile (1.0 mL). The solution was stirred for 18 h at 30° C. and an additional equivalent of DBU (40 microL, 0.26 mmol) was added to the solution, followed by 1-methylpiperazine (146 microL, 1.32 mmol). The mixture was heated to 60° C. for 1 h then concentrated in vacuo. The residue was partitioned between saturated aqueous NaHCO₃ and methylene chloride. The aqueous layer was extracted with methylene chloride. The combined organic extracts were dried over sodium sulfate, filtered and concentrated in vacuo. The residue was purified by semi-prep HPLC to provide the title compound, (22 mg, 16%) as a white solid (•3TFA salt): mp: 72-74° C. (dec.); ESI MS m/z 530 $[C_{29}H_{35}N_7O_3+H]^+$; HPLC>95%, $t_R$=13.68 min.

Example 3

Synthesis of 1-methyl-7-(pyridine-4-yloxy)-1H-indole-2-carboxylic acid (5-tert-butyl-2-methanesulfinyl-phenyl)-amide

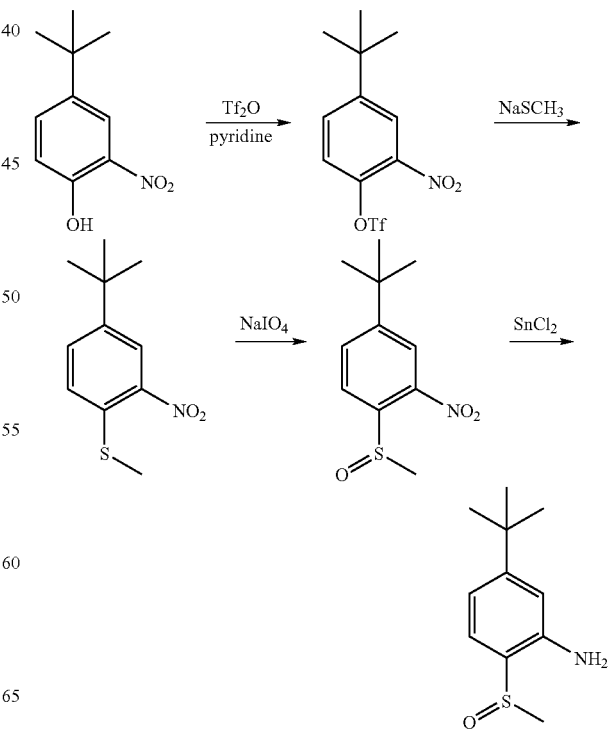

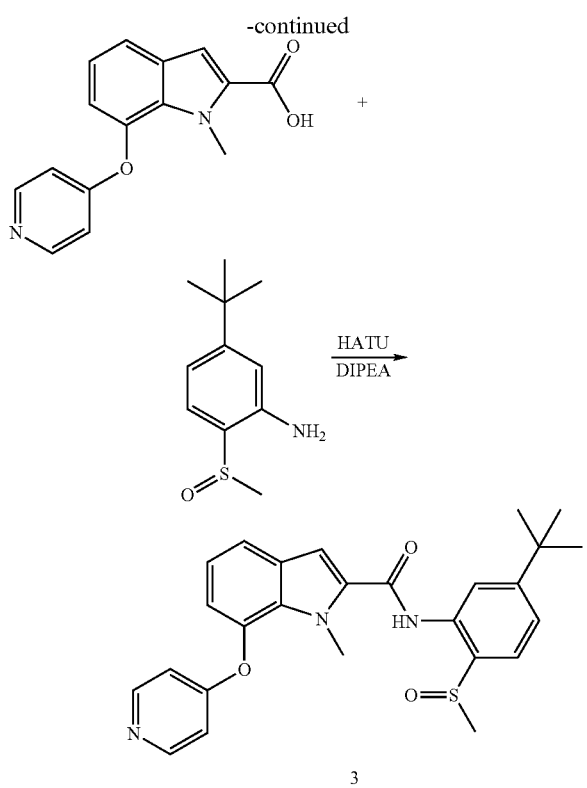

Triflic anhydride (4.14 mL, 24.6 mmol) was added dropwise to a solution of 4-tert-butyl-2-nitrophenol (4.00 g, 20.5 mmol) and pyridine (2.16 mL, 26.7 mmol) in methylene chloride (50 mL) at 0° C. The yellow solution was stirred 0.25 h at 0° C., poured onto saturated aqueous NaHCO₃ and extracted with methylene chloride. The combined extracts were washed with saturated aqueous NaHCO₃, dried over sodium sulfate, filtered, and concentrated in vacuo. The residue was purified by filtration through a plug of silica-gel (methylene chloride) to provide trifluoro-methanesulfonic acid 4-tert-butyl-2-nitro-phenyl ester (5.82 g, 87%) as a pale yellow oil which was utilized without further purification.

Sodium thiomethoxide (1.86 g, 26.6 mmol) was added to a cooled solution of the above triflate (5.80 g, 17.7 mmol) in DMF (35 mL) at 0° C. The red solution was warmed to room temperature and stirred at that temperature for 0.75 h, poured onto saturated aqueous NaHCO₃ and the aqueous layer was extracted with hexane. The combined extracts were washed with saturated aqueous NaHCO₃, dried over sodium sulfate, filtered, and concentrated in vacuo to provide a mixture (1:1) of the desired product and starting phenol. The residue was purified recrystallization from hexane to provide a yellow precipitate which was filtered off and washed with hexane. The remaining filtrate was concentrated in vacuo and repurified by silica-gel chromatography (3% diethyl ether in hexanes). The purified products were combined to provide 4-tert-butyl-1-methylsulfanyl-2-nitro-benzene (2.19 g, 55%) as a bright yellow solid.

Sodium periodate (1.23 g, 5.76 mmol) in water (2.0 mL) was added to a solution of the above thioether (1.08 g, 4.80 mmol) in methanol/THF (2:1, 15 mL). The mixture was stirred at 50° C. for 24 h, then the solvent was concentrated in vacuo. The residue was diluted with diethyl ether and washed with water and saturated aqueous NaHCO₃, dried over sodium sulfate, filtered, and concentrated in vacuo. Purification of the crude product by silica-gel chromatography (methylene chloride—50% ethyl acetate in methylene chloride) provided 4-tert-butyl-1-methanesulfinyl-2-nitro-benzene (1.05 g, 91%) as a white solid.

Tin(II) chloride dihydrate (2.84 g, 12.6 mmol) was added to a solution of the above sulfoxide (1.01 g, 4.19 mmol) in ethyl acetate (20 mL). The mixture was heated to reflux for 0.25 h upon which the solution became red in color. The solution was cooled to room temperature and poured onto aqueous 2.0 M NaOH. The aqueous phase was extracted with diethyl ether and the combined organic layers were washed with saturated aqueous NaHCO₃. The combined organic extracts were dried over sodium sulfate, filtered and concentrated in vacuo. The residue was redissolved in diethyl ether and extracted (3×) with 1.0 M HCl. The pH of the combined aqueous layers was adjusted to pH=10 with NaHCO₃ and extracted with methylene chloride. The combined organic layers were dried over sodium sulfate, filtered and concentrated in vacuo to provide 5-tert-butyl-2-methanesulfinyl-phenylamine (693 mg, 78%) as a white solid.

1-Methyl-7-(pyridine-4-yloxy)-1H-indole-2-carboxylic acid (127 mg, 0.473 mmol) and HATU (180 mg, 0.473 mmol) were combined in DMF (900 microL) and stirred for 5 min at room temperature. The above aniline (100 mg, 0.473 mmol) was added to the reaction mixture followed by N,N-diisopropylethylamine (247 microL, 1.42 mmol). The solution was stirred at room temperature for 18 h then poured onto saturated aqueous NaHCO₃. The aqueous layer was extracted with methylene chloride and the combined extracts were dried over sodium sulfate, filtered, and concentrated in vacuo. Purification by silica-gel chromatography (diethyl ether—1% methanol in diethyl ether) provided the title compound, in 92% purity. Trituration with diethyl ether provided pure 1-methyl-7-(pyridine-4-yloxy)-1H-indole-2-carboxylic acid (5-tert-butyl-2-methanesulfinyl-phenyl)-amide (63 mg, 33%) as a white solid, mp: 88-92° C. (dec.); ESI MS m/z 462 [$C_{26}H_{27}N_3O_3S$+H]⁺; HPLC>96%, $t_R$=15.89 min.

Example 4

Synthesis of 1-methyl-7-(pyridine-4-yloxy)-1H-indole-2-carboxylic acid (5-tert-butyl-2-methanesulfonyl-phenyl)-amide

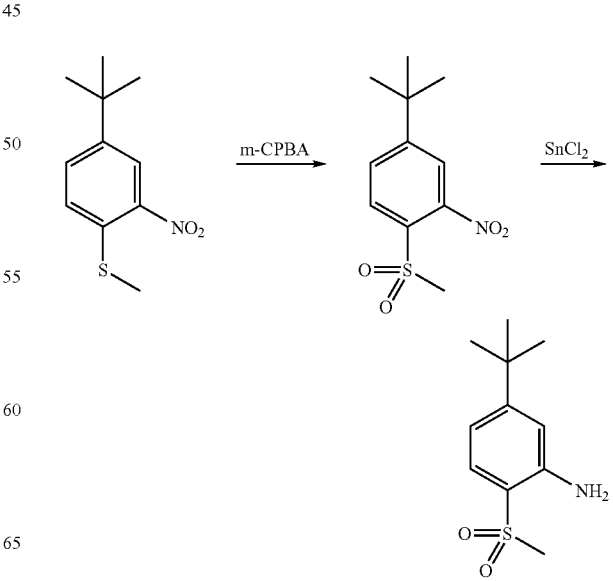

34%) as a white solid: mp: 158-159° C. (dec.); ESI MS m/z 478 [$C_{26}H_{27}N_3O_4S$+H]$^+$; HPLC>97%, $t_R$=18.07 min.

Example 5

Synthesis of 1-methyl-7-(pyridine-4-yloxy)-1H-indole-2-carboxylic acid (5-tert-butyl-2-oxo-1,2-dihydropyridin-3-yl)-amide

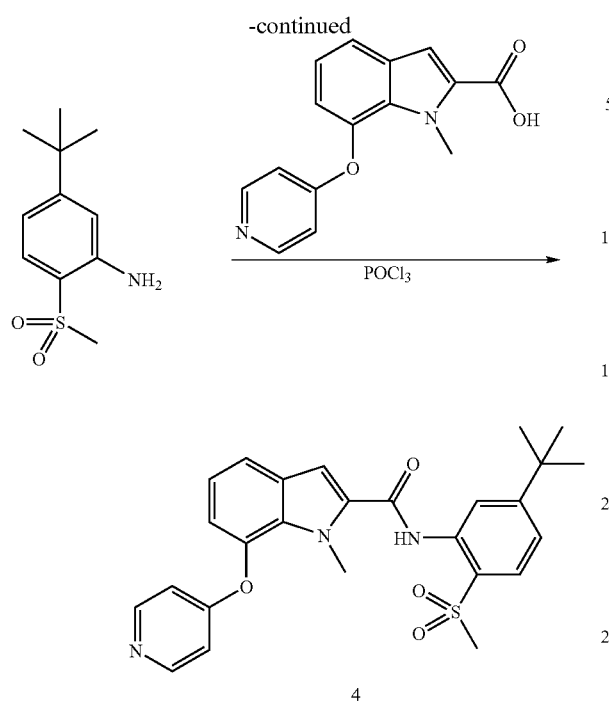

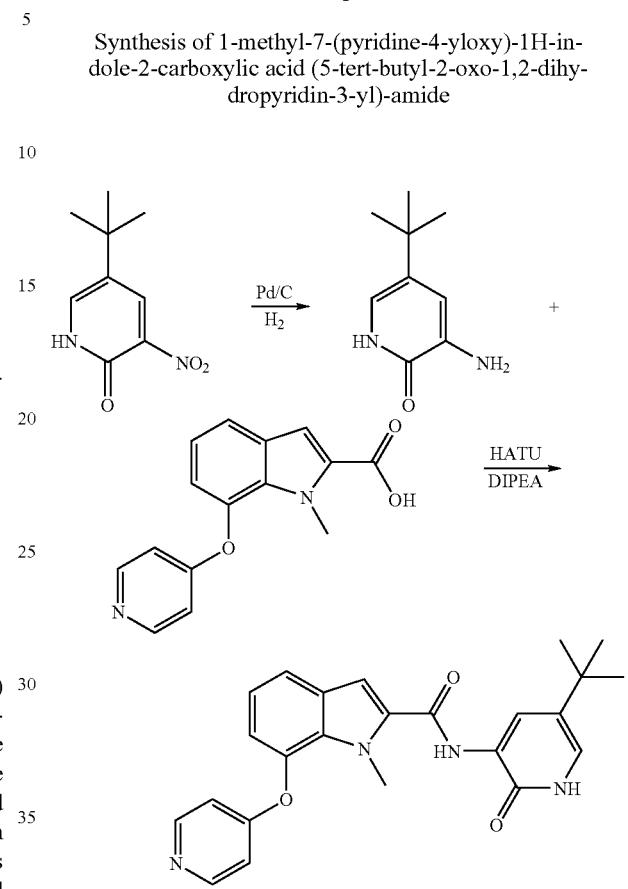

3-Chloroperoxybenzoic acid (77%, 1.84 g, 10.6 mmol) was added to a solution of 4-tert-butyl-1-methylsulfanyl-2-nitro-benzene (800 mg, 3.55 mmol) in methylene chloride (7.0 mL) at 0° C. The mixture was stirred at room temperature for 5 h, diluted with diethyl ether and poured onto saturated aqueous NaHCO$_3$. The organic layer was washed twice with saturated aqueous NaHCO$_3$, twice with saturated aqueous Na$_2$CO$_3$, dried over sodium sulfate, filtered, and concentrated in vacuo. Purification by silica-gel chromatography (20% ethyl acetate in hexane) provided 4-tert-butyl-1-methanesulfonyl-2-nitro-benzene (781 mg, 86%) as a white solid.

Tin(II) chloride dihydrate (2.73 g, 12.1 mmol) was added to a solution of the above sulfone (777 mg, 3.02 mmol) in ethyl acetate (15 mL). The mixture was heated to reflux for 0.5 h then cooled to room temperature and poured onto aqueous 2.0 M NaOH. The aqueous phase was extracted with diethyl ether and the combined organic layers were washed with saturated aqueous NaHCO$_3$, dried over sodium sulfate, filtered and concentrated in vacuo to provide pure 5-tert-butyl-2-methanesulfonyl-phenylamine (618 mg, 90%) as a white solid.

1-Methyl-7-(pyridine-4-yloxy)-1H-indole-2-carboxylic acid (47 mg, 0.177 mmol) and the above aniline (50 mg, 0.194 mmol) were dissolved in pyridine (600 microL) at room temperature. Phosphorus oxychloride (18 micro L, 0.194 mmol) was added dropwise to the solution and the reaction mixture was stirred at room temperature for 0.5 h. The solvent was concentrated and the residue was partitioned between saturated aqueous NaHCO$_3$ and methylene chloride. The aqueous layer was extracted with methylene chloride and the combined organic extracts were dried over sodium sulfate, filtered, and concentrated in vacuo. Purification by silica-gel chromatography (1% methanol in diethyl ether) provided 1-methyl-7-(pyridine-4-yloxy)-1H-indole-2-carboxylic acid (5-tert-butyl-2-methanesulfonyl-phenyl)-amide (54 mg, 3-Nitro-5-tert-butyl-1H-pyridin-2-one (360 mg, 1.83 mmol) was dissolved in methanol/ethyl acetate (2:1, 3 mL) and placed in a Parr hydrogenation vessel. Pd (10% on carbon, 36 mg) was added and the reaction was placed under a hydrogen atmosphere (50 psi) and shaken at room temperature for 2 h. The solution was then filtered through diatomaceous earth and concentrated in vacuo. The residue was redissolved in diethyl ether and extracted (3×) with 1.0 M HCl. The pH of the combined aqueous layers was adjusted to 10 with NaHCO$_3$ and extracted with methylene chloride. The combined organic layers were dried over sodium sulfate, filtered and concentrated in vacuo to provide 3-amino-5-tert-butyl-1H-pyridin-2-one (195 mg, 64%) as a pale green solid: ESI MS m/z 166 [$C_9H_{14}N_2O$+H]$^+$.

1-Methyl-7-(pyridine-4-yloxy)-1H-indole-2-carboxylic acid (145 mg, 0.542 mmol) and HATU (206 mg, 0.542 mmol) were combined in DMF (1 mL) and stirred 5 min at room temperature. The above aminopyridinone (90 mg, 0.542 mmol) was added to the reaction mixture followed by N,N-diisopropylethylamine (283 microL, 1.63 mmol). The solution was stirred at room temperature for 72 h then poured into saturated aqueous NaHCO$_3$. The aqueous layer was extracted with chloroform and the combined extracts were dried over sodium sulfate, filtered, and concentrated in vacuo. Purification by silica-gel chromatography (2% ammonium hydroxide, 50% ethyl acetate in hexane) provided 1-methyl-7-(pyridine-4-yloxy)-1H-indole-2-carboxylic acid (5-tert-butyl-2- oxo-1,2-dihydropyridin-3-yl)-amide (163 mg, 73%) as a white solid: mp: 236-238° C. (dec.); ESI MS m/z 417 $[C_{24}H_{24}N_4O_3+H]^+$; HPLC>97%, $t_R$=14.74 min.

Example 6

Synthesis of 1-methyl-7-(pyridine-4-yloxy)-1H-indole-2-carboxylic acid (5-tert-butyl-1-methyl-2-oxo-1,2-dihydropyridin-3-yl)-amide

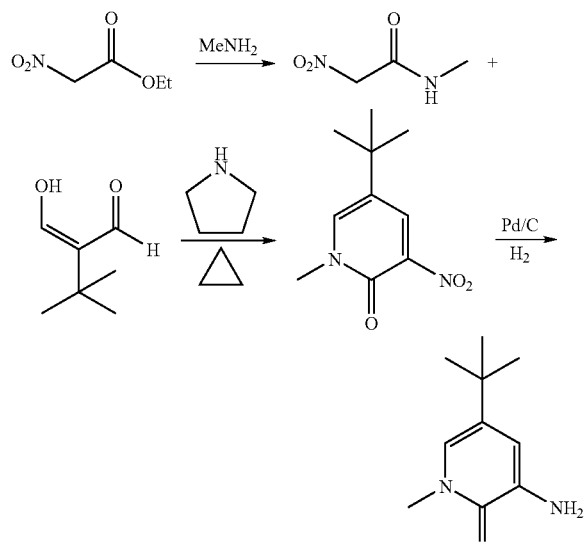

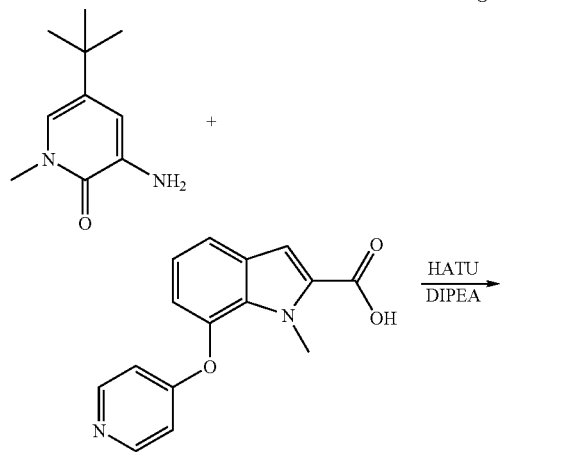

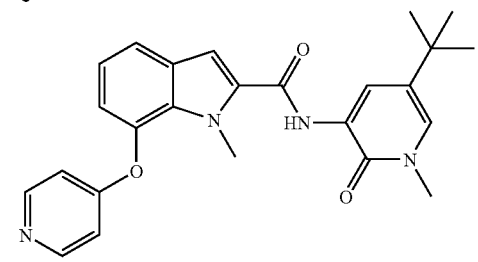

Ethyl nitroacetate (1.64 g, 12.3 mmol) was added to a solution of methylamine (33% in methanol, 7.7 mL, 61.6 mmol) and the solution was stirred at room temperature for 18 h.

The solvent was concentrated in vacuo and the residue was dissolved in aqueous 1.0 M HCl. The aqueous layer was washed with diethyl ether and the organic washings were discarded. The aqueous layer was then extracted with ethyl acetate and the combined organic layers were dried over sodium sulfate, filtered and concentrated in vacuo to provide N-methyl-2-nitro-acetamide (961 mg, 66%) as a pale yellow solid.

To a solution of 2-tert-butyl-malonaldehyde (385 mg, 3.00 mmol) and the above amide (355 mg, 3.00 mmol) dissolved in ethanol (6.0 mL) was added pyrrolidine (63 microL, 0.750 mmol). The mixture was heated at reflux for 18 h and concentrated in vacuo. Purification by silica-gel chromatography (75% ethyl acetate in hexanes) provided 5-tert-butyl-1-methyl-3-nitro-1H-pyridin-2-one (186 mg, 30%) as an orange solid.

The above nitro pyridine (186 mg, 0.886 mmol) was dissolved in methanol/ethyl acetate (2:1, 3 mL) and placed in a Parr hydrogenation vessel. Pd (10% on carbon, 20 mg) was added and the reaction was placed under a hydrogen atmosphere (50 psi) and shaken at room temperature for 1 h. The solution was then filtered through diatomaceous earth and concentrated in vacuo. The residue was redissolved in diethyl ether and extracted (3x) with 1.0 M HCl. The pH of the combined aqueous layers was adjusted to 10 with NaHCO$_3$ and extracted with methylene chloride. The combined organic layers were dried over sodium sulfate, filtered and concentrated in vacuo to provide 3-amino-5-tert-butyl-1-methyl-1H-pyridin-2-one (110 mg, 69%) as a blue solid: $^1$ESI MS m/z 180 $[C_{10}H_{16}N_2O_3+H]^+$.

1-Methyl-7-(pyridine-4-yloxy)-1H-indole-2-carboxylic acid (125 mg, 0.466 mmol) and the above aminopyridinone (84 mg, 0.466 mmol) were dissolved in pyridine (1.5 mL) at room temperature. Phosphorus oxychloride (48 micro L, 0.513 mmol) was added dropwise to the solution and the reaction mixture was stirred at room temperature for 0.5 h. The solvent was concentrated in vacuo and the residue was partitioned between saturated aqueous NaHCO$_3$ and methylene chloride. The aqueous layer was extracted with methylene chloride and the combined organic extracts were dried over sodium sulfate, filtered, and concentrated in vacuo. Purification by silica-gel chromatography (50% ethyl acetate in methylene chloride) provided 1-methyl-7-(pyridine-4-yloxy)-1H-indole-2-carboxylic acid (5-tert-butyl-1-methyl-2-oxo-1,2-dihydropyridin-3-yl)-amide (65 mg, 33%) as a pale pink solid: mp: 74-76° C. (dec.); ESI MS m/z 431 $[C_{25}H_{26}N_4O_3+H]^+$; HPLC>97%, $t_R$=15.69 min.

Example 7

Synthesis of 1-methyl-7-(pyridine-4-yloxy)-1H-indole-2-carboxylic acid (5-tert-butyl-2-methyl-pyridin-3-yl)-amide

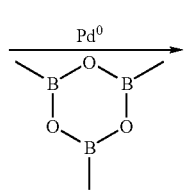

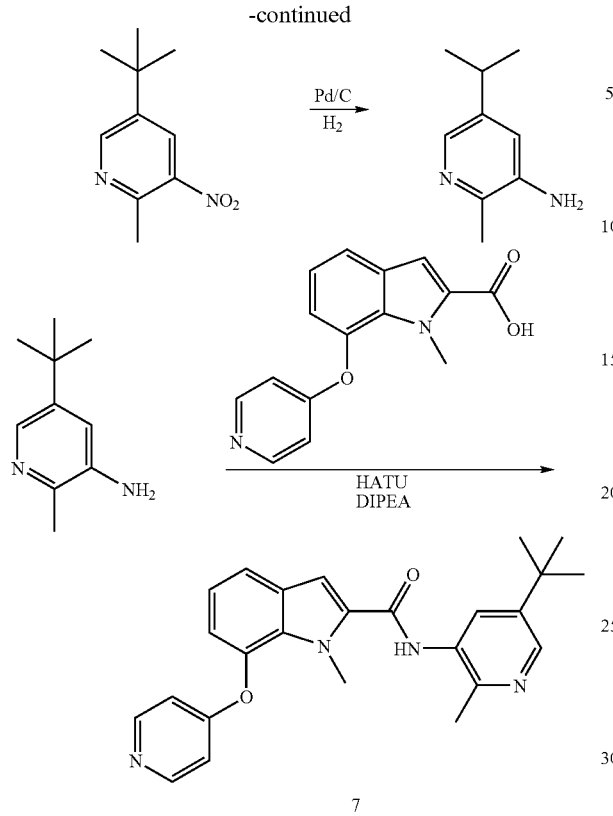

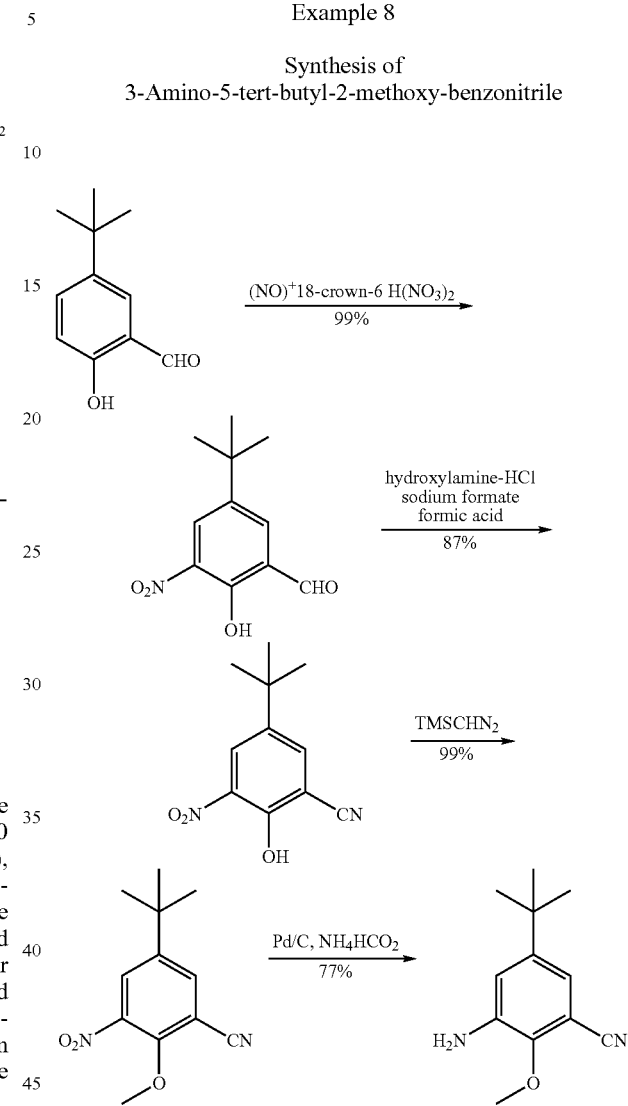

lic acid (5-tert-butyl-2-methyl-pyridin-3-yl)-amide (163 mg, 63%) as a pale yellow solid: mp: 52-56° C. (dec.); ESI MS m/z 415 $[C_{25}H_{26}N_4O_2+H]^+$; HPLC>95%, $t_R$=12.29 min.

Example 8

Synthesis of 3-Amino-5-tert-butyl-2-methoxy-benzonitrile

To a solution of 5-tert-butyl-2-chloro-3-nitro-pyridine (554 mg, 2.58 mmol) dissolved in 10% aqueous dioxane (5.0 mL) was added potassium carbonate (1.07 g, 7.74 mmol), trimethylboroxine (395 mL, 2.84 mmol), and lastly tetrakis-(triphenylphosphine)palladium (149 mg, 0.129 mmol). The solution was heated in a sealed tube to 100° C. for 18 h, cooled to room temperature and diluted with ether. The organic layer was washed twice with saturated aqueous NaHCO$_3$, dried over sodium sulfate, filtered, and concentrated in vacuo. Purification by silica-gel chromatography (10% ethyl acetate in hexane) provided 5-tert-butyl-2-methyl-3-nitro-pyridine (388 mg, 75%) as colorless oil.

The above pyridine (388 mg, 1.99 mmol) was dissolved in ethanol (6 mL) and placed in a Parr hydrogenation vessel. Pd (10% on carbon, 20 mg) was added and the reaction was placed under a hydrogen atmosphere (50 psi) and shaken at room temperature for 18 h. The solution was then filtered through diatomaceous earth, concentrated in vacuo to provide 5-tert-butyl-2-methyl-pyridin-3-ylamine (340 mg, 99%) as a pale orange solid: ESI MS m/z 164 $[C_{10}H_{16}N_2+H]^+$.

1-Methyl-7-(pyridine-4-yloxy)-1H-indole-2-carboxylic acid (183 mg, 0.683 mmol) and HATU (259 mg, 0.683 mmol) were combined in DMF (1.2 mL) and stirred 5 min at room temperature. The above aminopyridine (102 mg, 0.621 mmol) was added to the reaction mixture followed by N,N-diisopropylethylamine (326 microL, 1.86 mmol). The solution was stirred at room temperature for 18 h then poured onto saturated aqueous NaHCO$_3$. The aqueous layer was extracted with methylene chloride and the combined extracts were dried over sodium sulfate, filtered, and concentrated in vacuo. Purification by silica-gel chromatography (1% ammonium hydroxide, 50% ethyl acetate in methylene chloride) provided 1-methyl-7-(pyridine-4-yloxy)-1H-indole-2-carboxy- To a solution of 5-tert-butyl-2-hydroxybenzaldehyde (1.25 g, 7.0 mmol) in ethyl acetate (15 mL) was added (NO)$^+$18-crown-6.H(NO$_3$)$_2$ (2.64 g, 6.3 mmol). The solution turned yellow and was stirred at room temperature for 5 h. The solvent was evaporated, giving a residue which was taken up in ether. The ether was washed 4× with saturated NH$_4$Cl, dried over Na$_2$SO$_4$, filtered, and concentrated in vacuo to give 5-tert-butyl-2-hydroxyl-3-nitro-benzaldehyde (1.56 g, 99%) as a yellow solid.

The above aldehyde (1.4 g, 6.3 mmol), hydroxylamine hydrochloride (0.438 g, 6.3 mmol), and sodium formate (0.771 g, 11.3 mmol) in formic acid (20 mL) were heated overnight, at reflux, then cooled to room temperature. The reaction was diluted with water, and the resulting precipitate was filtered. The solid was taken up in ether, dried over Na$_2$SO$_4$, filtered and concentrated in vacuo to yield 5-tert-butyl-2-hydroxyl-3-nitro-benzonitrile (1.21 g, 87%) as a yellow solid.

The above nitrile (0.5 g, 2.27 mmol) was taken up in 1:9 methanol/acetonitrile (20 mL). N,N-diisopropylethylamine (1.1 mL, 6.35 mmol) was added dropwise followed by (trimethylsilyl)diazomethane (3.2 mL, 6.35 mmol). The reaction was stirred until the bubbling stopped (20 min) and the reaction was quenched with water. The water was extracted 3× with methylene chloride, dried over Na$_2$SO$_4$, filtered, and concentrated in vacuo to give 5-tert-butyl-2-methoxy-3-nitro-benzonitrile (0.531 g, 99%) as a yellow solid.

The above benzonitrile (100 mg, 0.427 mmol) was dissolved in 1:1 ethyl acetate/methanol (10 mL) in a nitrogen-flushed flask. Ammonium formate (270 mg, 4.27 mmol) and palladium on carbon (30 mg, 10% wet) were added and the mixture was heated to reflux for 30 min. The reaction was cooled to room temperature and filtered through a pad of diatomaceous earth, eluting with ethyl acetate. The ethyl acetate was evaporated under vacuum. The resulting residue was purified by chromatography on silica gel (1:1 ethyl acetate/hexanes) to afford the title compound, (67 mg, 77%) as a colorless oil.

Example 9

Synthesis of
6-tert-butyl-3-methoxy-pyridine-2,4-diamine droxy-isonicotinic acid ethyl ester (2.74 g, 96%) as a pale yellow oil which was utilized without further purification.

To a solution of the above bromopyridine (2.74 g, 9.07 mmol) in acetonitrile/methanol (9:1, 33 mL) was added N,N-diisopropylethylamine (2.50 mL, 14.2 mmol) followed by (trimethylsilyl)diazomethane (2.0M in hexane, 7.0 mL, 14.2 mmol). The red solution was stirred 0.5 h at room temperature then concentrated in vacuo. The residue was dissolved in methylene chloride, washed with saturated aqueous NaHCO$_3$, dried over sodium sulfate, filtered, and concentrated in vacuo to provide 2-bromo-6-tert-butyl-3-methoxy-isonicotinic acid ethyl ester (2.65 g, 93%) as a red oil which was utilized without further purification.

To a solution of the above bromide (2.65 g, 8.39 mmol) in DMF (18 mL) was added copper(I) cyanide (3.8 g, 42 mmol). The mixture was heated to 100° C. for 18 h then cooled to room temperature. The resultant black solution was poured into saturated aqueous NaHCO$_3$ and the aqueous layer was extracted with diethyl ether. The combined organic extracts were washed with saturated aqueous NaHCO$_3$, dried over sodium sulfate, filtered through a plug of silica gel (methylene chloride), and concentrated in vacuo to provide 6-tert-

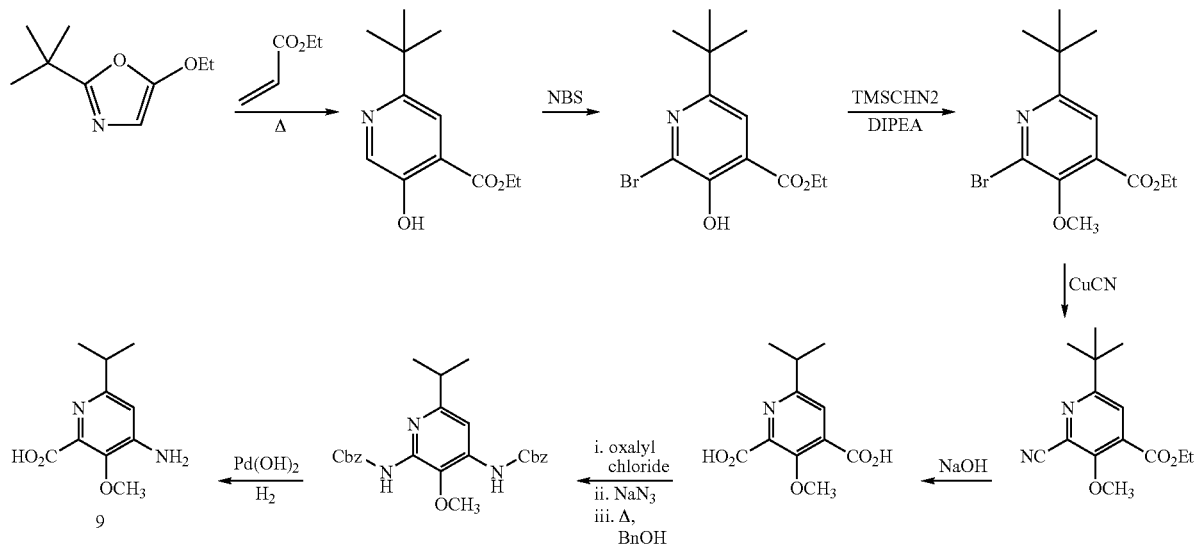

2-tert-Butyl-5-ethoxy-oxazole (16.6 g, 98.1 mmol) was dissolved in freshly distilled ethyl acrylate (11.7 mL, 108 mmol). The solution was heated in a sealed tube to 100° C. for 24 h. Upon cooling, the remaining starting materials were distilled away from the product which was further purified by filtration through a plug of silica-gel (methylene chloride) and concentrated to provide 2-tert-butyl-5-hydroxy-isonicotinic acid ethyl ester (11.2 g, 54%) as a pale yellow oil.

To a solution of the above isonicotinic acid ethyl ester (2.0 g, 9.47 mmol) in DMF (20 mL) was added N-bromosuccinimide (1.85 g, 10.4 mmol). The solution was stirred at room temperature for 0.5 h then poured into saturated aqueous NaHCO$_3$. The aqueous layer was extracted with diethyl ether and the combined organic layers were washed with saturated aqueous NaHCO$_3$, dried over sodium sulfate, filtered, and concentrated in vacuo to provide 2-bromo-6-tert-butyl-3-hybutyl-2-cyano-3-methoxy-isonicotinic acid ethyl ester (1.55 g, 70%) as a yellow oil which was utilized without further purification.

To a solution of the above nitrile (616 mg, 2.35 mmol) in ethanol (8.0 mL) was added NaOH (2.0 M in water, 8.3 mL, 16.5 mmol). The mixture was heated to reflux for 20 h then cooled to room temperature and the ethanol was concentrated in vacuo. The basic solution was neutralized with 12 N HCl to a pH=6 then extracted with chloroform/isopropanol (3:1). The combined organic extracts were dried over sodium sulfate, filtered, and concentrated in vacuo to provide 6-tert-butyl-3-methoxy-pyridine-2,4-dicarboxylic acid (402 mg, 68%) as a yellow solid which was utilized without further purification.

To a solution of the above diacid (123 mg, 0.49 mmol) in methylene chloride/THF (3:1, 1.0 mL) was added oxalyl chloride (104 microL, 1.21 mmol) followed by 1 drop of DMF. The solution initially bubbled and was stirred at room temperature for 3 h, then concentrated in vacuo. The residue was dissolved in dry acetone (1.0 mL) and a solution of sodium azide (2 M in water, 1.45 mL, 3.9 mmol) was added all at once. The mixture was immediately poured onto water and the aqueous layer extracted with methylene chloride. To the combined extracts was added toluene (4.0 mL) and the organic layer was dried over sodium sulfate, filtered, and concentrated in vacuo to approximately 1 mL of toluene remaining. An additional amount of toluene (5.0 mL) was added and this was again concentrated in vacuo to about 1.0 mL of toluene remaining. The resulting solution of diacyl azide was added dropwise to a refluxing solution of benzyl alcohol (116 microL, 1.12 mmol) in toluene (1.0 mL) which immediately evolved nitrogen. After heating the solution at reflux for 2 h, the mixture was cooled to room temperature and concentrated in vacuo to provide (4-benzyloxycarbonylamino-6-tert-butyl-3-methoxy-pyridin-2-yl)-carbamic acid benzyl ester.

To a solution of the crude dicarbamate from above in ethanol (3.0 mL) was added Pd(OH)$_2$ (20% on carbon, 20 mg). The mixture was placed in a Parr shaker and hydrogenated (50 psi) for 18 h. The solution was filtered and concentrated in vacuo. The resultant residue was purified by silica gel chromatography (1% concentrated ammonium hydroxide-5% methanol in chloroform) to provide the title compound, (43 mg, 45% over 2 steps) as a white solid: ESI MS m/z 196 [C$_{10}$H$_{17}$N$_3$O+H].

Example 10

Synthesis of 1-methyl-7-(pyridin-4-yloxy)-1H-indole-2-carboxylic acid [5-tert-butyl-2-methoxy-3-(2-oxo-azetidin-1-yl)-phenyl]-amide

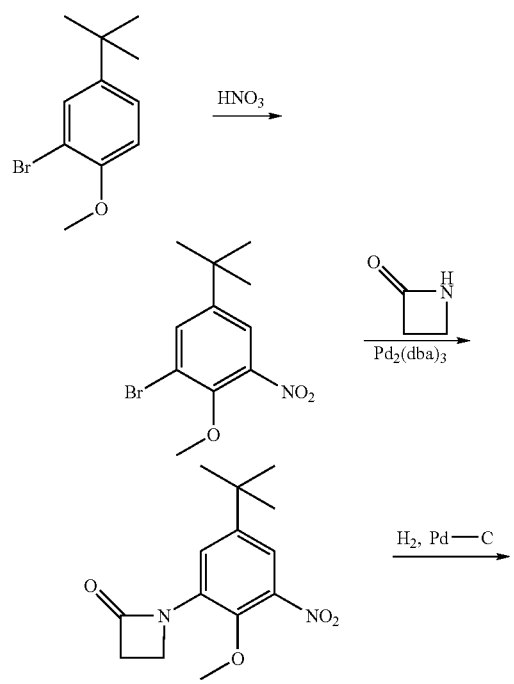

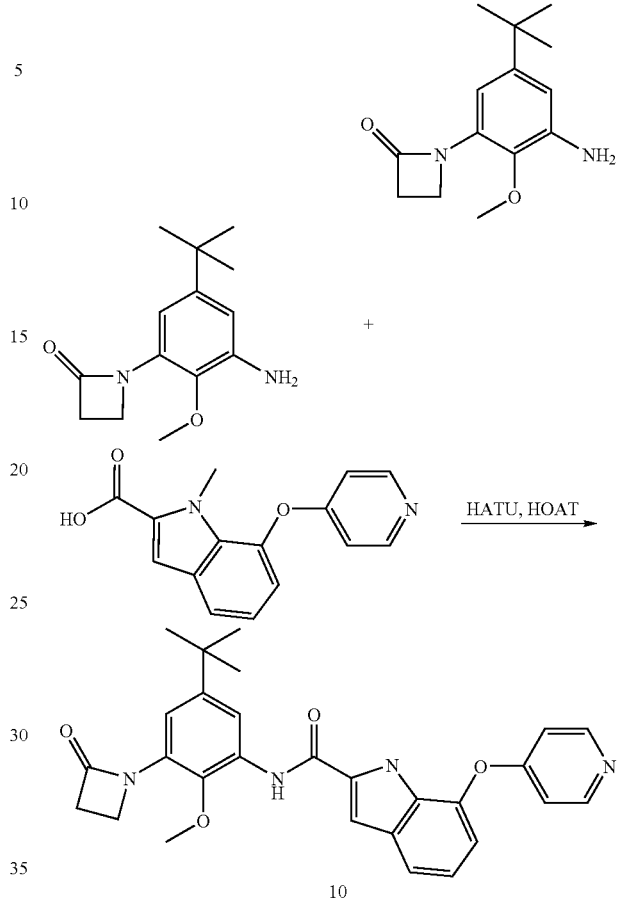

2-Bromo-4-tert-butylanisole (4.54 g, 18.67 mmol) was dissolved in acetic anhydride (15 mL) and the solution was cooled to 0° C. A solution of nitric acid (70%, 2.5 mL) in acetic anhydride (2.5 mL) was prepared by the dropwise addition of HNO$_3$ (70%, 2.5 mL) to Ac$_2$O at 0° C. The HNO$_3$ solution was pre-cooled to 0° C., and added dropwise to the stirred solution of the 2-bromo-4-tert-butylanisole over 5 min. The mixture was stirred at 0° C. for 1 h, then allowed to warm to room temperature and stirred overnight. The reaction mixture was diluted with EtOAc (150 mL) and saturated NaHCO$_3$ (50 mL) This mixture was then neutralized by gradual addition of solid NaHCO$_3$ until the pH was between 7-8. The organic layer was separated, washed with brine (50 mL) and dried over anhydrous Na$_2$SO$_4$. The solvents were removed in vacuo, the residue was purified by column chromatography (eluting with 3:1 hexane-EtOAc) to give 2-bromo-4-tert-butyl-6-nitroanisole (2 g, 37%).

An oven-dried Schlenk tube was charged with the above nitroanisole (500 mg, 1.74 mmol), 2-azetidinone (150 mg, 2.1 mmol), tris(dibenzylideneacetone) dipalladium(0) (32 mg, 0.035 mmol), 4,5-bis(diphenylphosphino)-9,9-dimethylxanthene (58 mg, 0.1 mmol) and cesium carbonate (795 mg, 2.44 mmol). The tube was capped with a rubber septum, purged with argon and 1,4-dioxane (7 mL) was then added through the septum via a syringe. The tube was sealed with a teflon screwcap and the reaction mixture was stirred at 100° C. for 20 h. The reaction mixture was cooled to room temperature, diluted with EtOAc (100 mL), washed with water, brine and dried over anhydrous Na$_2$SO$_4$. The solvent was removed in vacuo, and the crude product was purified by column:chromatography (2:1 hexane-EtOAc) to give 1-(5-tert-butyl-2-methoxy-3-nitro-phenyl)-azetidin-2-one (516 mg, quantitative).

A mixture of the above coupled nitroanisole (250 mg, 0.90 mmol) and Pd (10% on carbon, 60 mg) in absolute EtOH (5 mL) was stirred under H$_2$ (1 atm) overnight. The reaction mixture was filtered through diatomaceous earth, and solid residue was rinsed with EtOAc (20 mL). The filtrate was concentrated in vacuo to give 1-(3-amino-5-tert-butyl-2-methoxy-phenyl)-azetidin-2-one (210 mg, 94%), which was used in next step without further purification.

To a suspension of 1-methyl-7-(pyridine-4-yloxy)-1H-indole-2-carboxylic acid (40 mg, 0.15 mmol) in DMF (1 mL) was added Hunig's base (52 microL, 0.3 mmol) resulting in a clear solution. After 5 min, HATU (90 mg, 0.23 mmol) and HOAT (3 mg, 0.02 mmol) were added followed by the above anisidine (37 mg, 0.15 mmol). The mixture was stirred overnight. The reaction mixture was diluted with EtOAc (30 mL), washed with water, brine, dried over anhydrous Na$_2$SO$_4$ and concentrated in vacuo. The crude product was purified by column chromatography (eluting with 30-80% EtOAc in hexane) to give the title compound (50 mg, 75%).

Example 11

Synthesis of 1-methyl-7-(pyridin-4-yloxy)-1H-indole-2-carboxylic acid [5-tert-butyl-2-methoxy-3-(2-oxo-pyrrolidin-1-yl)-phenyl]-amide

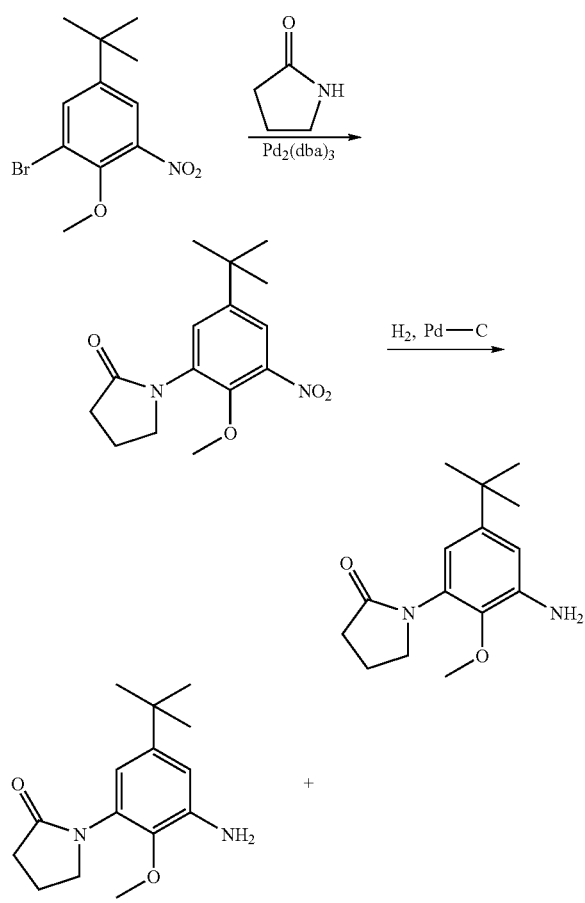

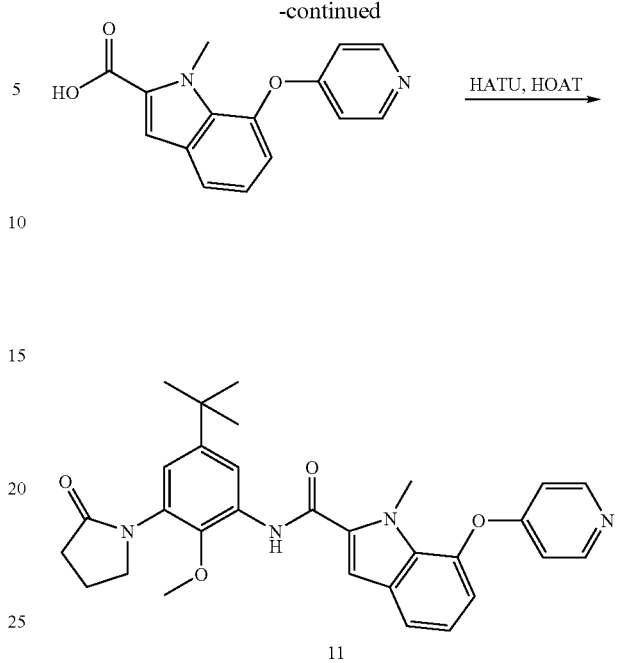

11

An oven-dried Schlenk tube was charged with 2-bromo-4-tert-butyl-6-nitroanisole (500 mg, 1.74 mmol), 2-pyrrolidinone (158 μL, 2.09 mmol), Pd$_2$(dba)$_3$ (32 mg, 0.035 mmol), 4,5-bis(diphenylphosphino)-9,9-dimethylxanthene (58 mg, 0.1 mmol) and Cs$_2$CO$_3$ (795 mg, 2.44 mmol). The tube was capped with a rubber septum, purged with argon and 1,4-dioxane (7 mL) was then added through the septum via a syringe. The tube was sealed with a teflon screwcap, and the reaction mixture was stirred at 100 C for 20 h. The reaction mixture was cooled to room temperature, diluted with EtOAc (100 mL), washed with water, brine and dried over anhydrous Na$_2$SO$_4$. The solvent was removed in vacuo, and crude product was purified by column chromatography (2:1 hexane-EtOAc) to give 1-(5-tert-butyl-2-methoxy-3-nitro-phenyl)-pyrrolidin-2-one (150 mg, 30%).

A mixture of the above coupled nitroanisole (145 mg, 0.50 mmol) and Pd (10% on carbon, 40 mg) in EtOAc (5 mL) was stirred under H$_2$ (1 atm) overnight. The reaction mixture was filtered through diatomaceous earth and solid residue was rinsed with EtOAc (20 mL). The filtrate was concentrated in vacuo to give 1-(3-amino-5-tert-butyl-2-methoxy-phenyl)-pyrrolidin-2-one (100 mg, 77%), which was used in the next step without further purification.

To a suspension of 1-methyl-7-(pyridine-4-yloxy)-1H-indole-2-carboxylic acid (40 mg, 0.15 mmol) in DMF (1 mL) was added Hunig's base (52 microL, 0.3 mmol) resulting in a clear solution. After 5 min, HATU (90 mg, 0.23 mmol) and HOAT (3 mg, 0.02 mmol) were added followed by the above anisidine (39 mg, 0.15 mmol). The mixture was stirred overnight. The reaction mixture was diluted with EtOAc (30 mL), washed with water, brine, dried over anhydrous Na$_2$SO$_4$ and concentrated in vacuo. The crude product was purified by column chromatography (eluting with 30-80% EtOAc in hexane) to give the title compound (60 mg, 78%).

Example 12

Synthesis of N-[3-amino-2-methoxy-5-(1-methylcyclopropyl)-phenyl]-methanesulfonamide

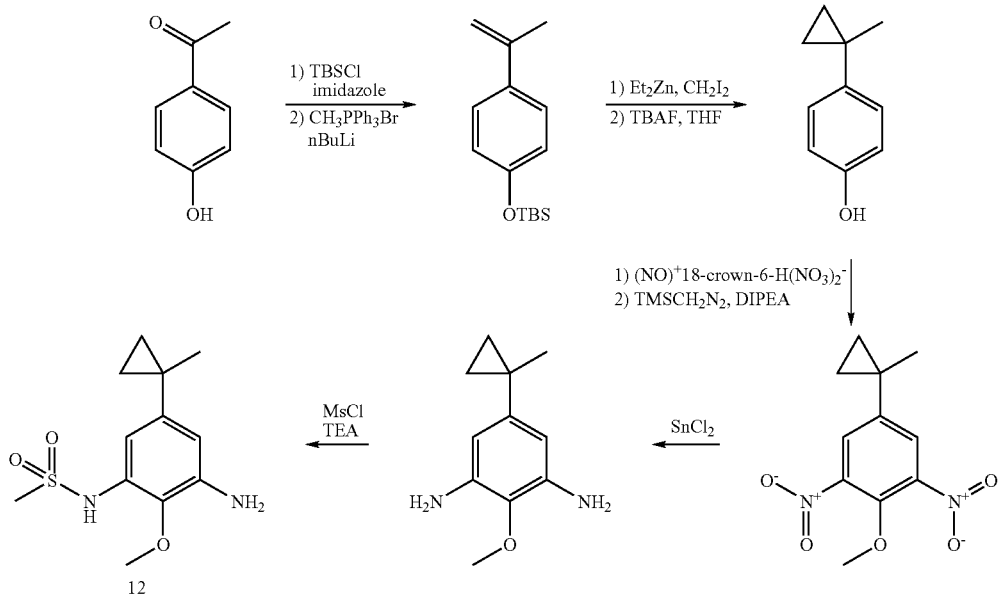

To a solution of 4-hydroxyacetophenone (10.0 g, 73.5 mmol) in DMF (74 mL) was added imidazole (12.0 g, 176.3 mmol) and tert-butyldimethylsilyl chloride (13.3 g, 88.1 mmol). The colorless solution was stirred for 0.75 h at room temperature then quenched with saturated aqueous NaHCO$_3$. The aqueous phase was extracted with hexanes and the combined organic layers were washed with saturated aqueous NaHCO$_3$. The organic layers were dried over sodium sulfate, filtered, and concentrated to provide the silyl ether (18.0 g, 98%) as a white solid which was utilized without further purification.

Methyl(triphenylphosphonium) bromide (17.1 g, 48.0 mmol) was suspended in THF (96 mL) and cooled to 0° C. n-Butyllithium (2.5 M in hexane, 19.2 mL, 48.0 mmol) was added dropwise to the mixture. The red solution was stirred at room temperature for 0.5 h. The acetophenone silyl ether (10.0 g, 40.0 mmol) from above was added. The solution turned bright yellow and a white precipitate formed. The mixture was stirred for 1 h at room temperature and then the solution was quenched with saturated aqueous NaHCO$_3$. The aqueous phase was extracted with diethyl ether and the combined organic layers were washed with saturated aqueous NaHCO$_3$. The organic layers were dried over sodium sulfate, filtered and concentrated. The resulting mixture was eluted through a plug of silica gel (hexanes) and the filtrate was concentrated to provide the styrene (8.36 g, 84%) as a colorless oil.

Diethylzinc (1.0 M in hexanes, 69 mL, 69 mmol) was added to a solution of the above styrene intermediate (6.85 g, 27.6 mmol) in dichloroethane at 0° C. Diiodomethane (11.2 mL, 138 mmol) was then added dropwise to the solution and the resulting mixture was stirred at 0° C. for 0.5 h and allowed to warm to room temperature for 2 h. The opaque mixture was quenched with saturated aqueous NH$_4$Cl. The aqueous phase was extracted with methylene chloride and the combined organic layers were washed with saturated aqueous NaHCO$_3$. The organic layers were dried over sodium sulfate, filtered through diatomaceous earth, and concentrated. The crude residue was dissolved in THF (50 mL) and TBAF (1.0 M in THF, 28 mL, 28 mmol) was added at room temperature. The solution was stirred for 2 h and then quenched with aqueous 1.0 M HCl. The aqueous phase was extracted with EtOAc and the combined organic layers were washed with saturated aqueous NaHCO$_3$. The organic layers were dried over sodium sulfate, filtered and concentrated. Purification by silica-gel chromatography (1% 2-propanol/12% EtOAc in hexanes) provided the phenol intermediate (2.77 g, 68%) as a white solid:

(NO)$_{1\text{-}8}$-crown-6.H(NO$_3$)$_2$[1] (18.0 g, 43.0 mmol) was added to a solution of the above phenol intermediate (2.77 g, 18.7 mmol) in EtOAc. The reaction mixture was heated to reflux for 5 min and then cooled to room temperature. The mixture was poured into aqueous 1.0 M HCl. The aqueous phase was extracted with diethyl ether. The combined organic layers were dried over sodium sulfate, filtered and concentrated. The residue was dissolved in acetonitrile/MeOH (9:1, 62 mL), cooled to 0° C. and N,N-diisopropylethylamine (13 mL, 74.8 mmol) was added slowly. The deep red solution was warmed to room temperature and trimethylsilyldiazomethane (2.0 M in hexane, 18.7 mL, 37.4 mmol) was added slowly to control nitrogen evolution. After stirring at room temperature for 0.5 h, the mixture was concentrated and partitioned between methylene chloride and saturated aqueous NH$_4$Cl. The aqueous layer was extracted with methylene chloride and the combined extracts were dried over sodium sulfate, filtered and concentrated. Purification by silica-gel chromatography (6% EtOAc in hexanes) provided the dinitroanisole (2.21 g, 47%) as a red oil.

Tin(II) chloride dihydrate (11.9 g, 52.6 mmol) was added to a solution of the above dinitroanisole (2.21 g, 8.76 mmol) in EtOAc (30 mL). The mixture was heated to reflux for 0.25 h upon which the solution became red in color. The solution was cooled to room temperature and poured into aqueous 2.0

M NaOH. The aqueous phase was extracted with EtOAc and the combined organic layers were washed with saturated aqueous NaHCO$_3$. The organic layers were dried over sodium sulfate, eluted through a plug of silica gel (1% ammonium hydroxide in methylene chloride), and the filtrate was concentrated. The residue was dissolved in diethyl ether and extracted (3×) with 1.0 M HCl. The pH of the combined aqueous layers was adjusted to pH=12 with 2.0 M NaOH and extracted with methylene chloride. The combined organic layers were dried over sodium sulfate, filtered and concentrated to provide diaminoanisole (860 mg, 52%) as a red oil.

Triethylamine (521 μL, 3.74 mmol) was added to a solution of the above diaminoanisole (718 mg, 3.74 mmol) in methylene chloride at −10° C. Methanesulfonyl chloride (290 μL, 3.74 mmol) was then added dropwise over a 10 min period and the resulting solution was allowed to slowly warm to room temperature over 2 h. The mixture was quenched with saturated aqueous NaHCO$_3$ and the aqueous layer was extracted with methylene chloride. The combined organic layers were dried over sodium sulfate, filtered and concentrated. Purification by silica gel chromatography (1% ammonium hydroxide/35% EtOAc in hexanes to 1% ammonium hydroxide/50% EtOAc in hexanes) provided a red solid which was triturated with diethyl ether/hexanes (1:1) to yield the title compound (510 mg, 51%) as a pale brown solid, mp 144-146° C.

This intermediate can then be coupled to the indole core and reacted further by the procedures described in the examples above, to form desired analogous indole amides.

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anticoagulant or fibrinolytic therapy (and the diseases or conditions related to such therapy) as described in the U.S. application Ser. No. 10/630,599.

The compounds of the invention are also p38 MAP kinase inhibitors. Activity can be demonstrated by using methods known in the art. See for example Branger et al., (2002) *J. Immunol.* 168: 4070-4077, and the 46 references cited therein, each incorporated herein by reference in their entirety. As disclosed in the Background of the Invention, the compounds of the invention will therefore be useful for treating inflammatory and oncological diseases. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US 01/21860 and U.S. application Ser. No. 10/214,782, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to U.S. application Ser. No. 10/313,667. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Biological Assays

Inhibition of TNF Production in THP Cells

The inhibition of cytokine production can be observed by measuring inhibition of TNFα in lipopolysaccharide stimulated THP cells (for example, see W. Prichett et al., 1995, *J Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was non-sterile. Initial stock solutions were made in DMSO followed by dilution into RPMI 1640 2-fold higher than the desired final assay concentration. Confluent THP.1 cells ($2\times10^6$ cells/ml, final conc.; American Type Culture Company, Rockville, Md.) were added to 96 well polypropylene round bottomed culture plates (Costar 3790; sterile) containing 125 µl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 µg/ml final; Siga L-2630, from *E. coli* serotype 0111.B4; stored as 1 mg/ml stock in endotoxin screened distilled $H_2O$ at −80° C.). Blanks (unstimulated) received $H_2O$ vehicle; final incubation volume was 250 µl. Overnight incubation (18-24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

Preferred compounds have an $IC_{50}<1$ uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, *Int. J. Immunopharmacol.*, 10, 835).

All references cited in this application are incorporated herein by reference in their entirety.

What is claimed is:

1. A compound of the formula (I)

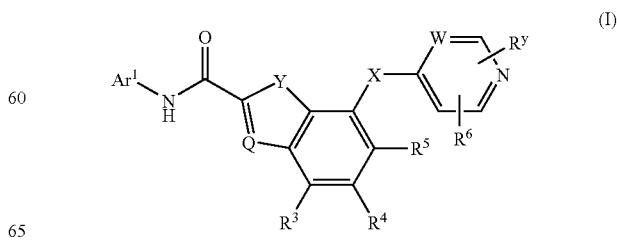

wherein:

Ar¹ is chosen from rings (i), (ii) and (iii) below:

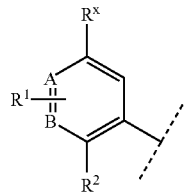
(i)

wherein one of A or B is nitrogen and the other is carbon, R¹ is covalently attached to either A or B, and when nitrogen is N—R¹ the double bond between A and B is not present;

$R_1$ is chosen from hydrogen, $NO_2$, —$N(R^c)_2$, J-C(O)—N$(R^c)$—, J-S(O)$_m$—N$(R^c)$—, or $R^1$ is chosen from $C_{1-6}$ alkyl, $C_{3-7}$ cylcoalkyl, $C_{1-5}$ alkoxyl or $C_{3-7}$ cycloalkoxyl, $C_{1-5}$ alkylthiol or $C_{3-7}$ cycloalkylthiol, $C_{1-5}$ acyl, $C_{1-5}$ alkoxycarbonyl, $C_{1-5}$ acyloxy, $C_{1-5}$ acylamino, $C_{2-5}$ alkenyl, $C_{2-5}$ alkynyl, heterocycle, heteroaryl and nitrile, each of the aforementioned where possible are optionally partially or fully halogenated or are optionally further substituted with alkylsulfonylamino, alkoxyl, amino, alkylamino, dialkylamino, hydroxyl, oxo, nitro or nitrile;

or $R^1$ is, where P can be O, >$CR^9$ or >$NR^9$

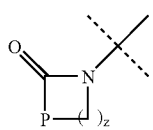

wherein z is 1 to 4;

$R^9$ is chosen from $C_{1-6}$ alkyl, $C_{3-7}$ cylcoalkyl, $C_{1-5}$ alkoxyl or $C_{3-7}$ cycloalkoxyl, $C_{1-5}$ alkylthiol or $C_{3-7}$ cycloalkylthiol, $C_{1-5}$ acyl, $C_{1-5}$ alkoxycarbonyl, $C_{1-5}$ acyloxy, $C_{1-5}$ acylamino, $C_{2-5}$ alkenyl, $C_{2-5}$ alkynyl, heterocycle, heteroaryl and nitrile, each of the aforementioned where possible are optionally partially or fully halogenated or are optionally further substituted with alkylsulfonylamino, alkoxyl, amino, alkylamino, dialkylamino, hydroxyl, oxo, nitro or nitrile;

$R^2$ is chosen from hydrogen, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl, oxo, $C_{1-5}$ alkylS(O)$_m$— and amino optionally mono- or di-substituted by $C_{1-5}$ alkyl, aryl or aryl $C_{1-5}$ alkyl;

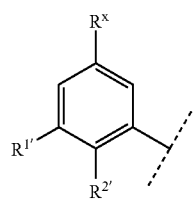
(ii)

wherein $R^{1'}$ is chosen from hydrogen, $C_{1-5}$ alkylS(O)$_m$—, $C_{1-6}$ alkyl, $C_{3-7}$ cylcoalkyl, $C_{1-5}$ alkoxyl or $C_{3-7}$ cycloalkoxyl, $C_{1-5}$ alkylthiol $C_{3-7}$ cycloalkylthiol, $C_{1-5}$ acyl, $C_{1-5}$ alkoxycarbonyl, $C_{1-5}$ acyloxy, $C_{2-5}$ alkenyl, $C_{2-5}$ alkynyl, heterocycle, heterocycle$C_{1-6}$ alkyl, heteroaryl, heteroaryl$C_{1-6}$ alkyl and nitrile, each of the aforementioned where possible are optionally partially or fully halogenated or are optionally further substituted with alkylsulfonylamino, alkoxyl, amino, alkylamino, dialkylamino, hydroxyl, oxo, nitro or nitrile;

$R^{2'}$, is chosen from nitrile, $C_{1-5}$ alkylS(O)$_m$—, J-O—C(O)—O—, $NH_2$—C(O)—(CH$_2$)$_n$—, H, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl and amino optionally mono- or di-substituted by $C_{1-5}$ alkyl, aryl or aryl $C_{1-5}$ alkyl;

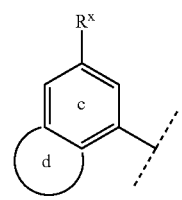
(iii)

wherein c is a benzo ring fused to ring d which is a 5-7 membered heterocyclic ring;

each $R^x$ is chosen from $C_{1-6}$ alkyl or $C_{3-7}$ cycloalkyl each being optionally substituted by $C_{1-3}$ alkyl and optionally partially or fully halogenated, $C_{1-4}$ acyl, aroyl, $C_{1-4}$ alkoxy, which may optionally be partially or fully halogenated, halogen, $C_{1-6}$ alkoxycarbonyl, carbocyclesulfonyl and —$SO_2$—$CF_3$;

each J is independently chosen from $C_{1-10}$ alkyl and carbocycle each optionally substituted by $R^b$;

$R^b$ is chosen from hydrogen, $C_{1-5}$ alkyl, hydroxy$C_{1-5}$ alkyl, $C_{2-5}$ alkenyl, $C_{2-5}$ alkynyl, carbocycle, heterocycle, heteroaryl, $C_{1-5}$ alkoxy, $C_{1-5}$ alkylthio, amino, $C_{1-5}$ alkylamino, $C_{1-5}$ dialkylamino, $C_{1-5}$ acyl, $C_{1-5}$ alkoxycarbonyl, $C_{1-5}$ acyloxy, $C_{1-5}$ acylamino, each of the aforementioned are optionally partially or fully halogenated, or $R^b$ is chosen from $C_{1-5}$ alkylsulphonylamino, hydroxy, oxo, halogen, nitro and nitrile;

Q is a N;

Y is >$CR^pR^v$, —$CR^p$=$C(R^v)$—, —O— or >$S(O)_m$;

each $R^c$, $R^p$, $R^V$ and $R^y$ are each independently hydrogen or $C_{1-5}$ alkyl;

X is —$CH_2$—, —$N(R^c)$—, —O— or —S—;

W is N or CH;

each m independently 0, 1 or 2;

n is 1-4;

each $R^3$, $R^4$ and $R^5$ are independently chosen from hydrogen, $C_{1-6}$ alkyl and halogen;

$R^6$ is optionally attached at a position ortho or meta to the N atom of the indicated ring, and is chosen from a bond, —O—, —O—(CH$_2$)$_{1-5}$—, >C(O), —NH—, —C(O)—NH—, —S—, $C_{1-5}$ alkyl branched or unbranched, $C_{2-5}$ alkenyl, $C_{1-3}$ acyl, $C_{1-3}$ alkyl(OH), heterocycle selected from morpholinyl, piperazinyl, piperidinyl, pyrrolidinyl and tetrahydrofuranyl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl and isothiazolyl or aryl each alkyl, alkenyl, acyl, heterocycle, heteroaryl and aryl are optionally substituted by one to three hydroxy, oxo, $C_{1-3}$ alkyl, $C_{1-3}$ alkoxy, $C_{1-5}$ alkoxycarbonyl, —$NR^7R^8$ or $NR^7R^8$—C(O)—;

wherein each $R^6$ is further optionally covalently attached to groups chosen from:

hydrogen, $NR^7R^8$, $C_{1-3}$ alkyl, $C_{3-6}$ cycloalkyl$C_{0-2}$alkyl, hydroxy, $C_{1-3}$ alkoxy, phenoxy, benzyloxy, aryl$C_{0-4}$ alkyl, heteroaryl $C_{0-4}$ alkyl and heterocycle $C_{0-4}$alkyl, each above-listed heterocycle, heteroaryl and aryl group is optionally substituted by one to three hydroxy, oxo, $C_{1-4}$ alkyl, $C_{1-3}$ alkoxy, $C_{1-5}$ alkoxycarbonyl, $NR^7R^8$—C(O)— or $C_{1-4}$ acyl;

each $R^7$ and $R^8$ are independently hydrogen, phenyl$C_{0-3}$alkyl optionally substituted by halogen, $C_{1-3}$ alkyl or di$C_{1-5}$ alkyl amino, or $R^7$ and $R^8$ are $C_{1-2}$ acyl, benzoyl or $C_{1-5}$ branched or unbranched alkyl optionally substituted by $C_{1-4}$ alkoxy, hydroxy or mono or di$C_{1-3}$ alkyl amino;

or the pharmaceutically acceptable salts thereof.

2. The compound according to claim 1 and wherein:

if $Ar^1$ is (i) then:

$R^1$ is chosen from hydrogen, $C_{1-6}$ alkyl, $C_{3-7}$ cylcoalkyl, $C_{1-5}$ alkoxyl and nitrile, each of the aforementioned where possible are optionally partially or fully halogenated or are optionally further substituted with alkylsulfonylamino, alkoxyl, amino, alkylamino, dialkylamino, hydroxyl, oxo, nitro or nitrile;

$R^2$ is chosen from hydrogen, halogen, $C_{1-5}$ alkyl, $C_{1-5}$ alkoxy, $C_{1-5}$ alkyl$C_{1-5}$ alkoxy, hydroxy, hydroxy $C_{1-5}$ alkyl, oxo, $C_{1-5}$ alkylS(O)$_m$— and amino optionally mono- or di-substituted by $C_{1-5}$ alkyl, phenyl or phenyl $C_{1-5}$ alkyl;

if $Ar^1$ is (ii) then:

$R^{1'}$ is chosen from H, $C_{1-6}$ alkyl, $C_{1-5}$ alkylS(O)$_m$—, $C_{1-5}$ alkoxyl $C_{1-5}$ alkylthiol, $NH_2$—C(O)—(CH$_2$)$_n$—, heterocycle, heterocycle$C_{1-6}$ alkyl, heteroaryl and nitrile, each of the aforementioned where possible are optionally partially or fully halogenated or are optionally further substituted with alkylsulfonylamino, alkoxyl, amino, alkylamino, dialkylamino, hydroxyl, oxo, nitro and nitrile;

$R^{2'}$ is chosen from $C_{1-5}$ alkylS(O)$_m$—, J-O—C(O)—O—, $C_{1-5}$ alkyl and $C_{1-5}$ alkoxy;

or if $Ar^1$ is (iii) then:

ring d is a 5-6 membered heterocyclic ring; and z is 1 to 2.

3. The compound according to claim 2 and wherein:

if $Ar^1$ is (i) then:

$R^1$ is chosen from hydrogen, $C_{1-6}$ alkyl or nitrile;

$R^2$ is chosen from hydrogen, halogen, $C_{1-5}$ alkyl, $C_{1-5}$ alkoxy, oxo or $C_{1-5}$ alkylS(O)$_m$—;

if $Ar^1$ is (ii) then:

$R^{1'}$ is chosen from hydrogen, $C_{1-6}$ alkyl, $C_{1-5}$ alkylS(O)$_m$—, $C_{1-5}$ alkoxyl $C_{1-5}$ alkylthiol, $NH_2$—C(O)—(CH$_2$)$_n$—, morpholino $C_{1-6}$ alkyl, heteroaryl chosen from pyrazole, triazole, imidazole and tetrazole, and nitrile;

$R^{2'}$ is chosen from $C_{1-5}$ alkylS(O)$_m$—, J-O—C(O)—O—, $C_{1-5}$ alkyl and $C_{1-5}$ alkoxy;

or if $Ar^1$ is (iii) then:

ring d is a 5-6 membered heterocyclic ring such that rings c and d fuse to form the following:

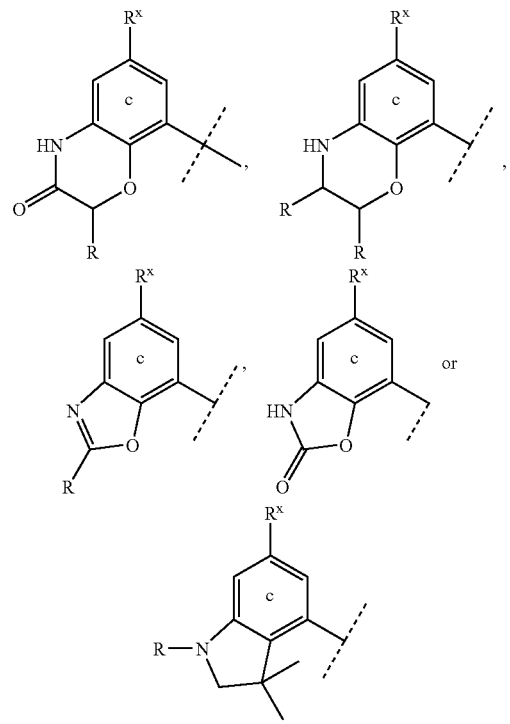

where each R is independently H or $C_{1-3}$ alkyl.

4. The compound according to claim 3 and wherein:

J is chosen from $C_{1-10}$ alkyl, aryl and $C_{3-7}$ cycloalkyl each optionally substituted by $R^b$;

$R^x$ is independently chosen from $C_{1-6}$ alkyl which may optionally be partially or fully halogenated, $C_{3-6}$ cycloalkyl optionally substituted by $C_{1-3}$ alkyl and optionally partially or fully halogenated, acetyl, aroyl, $C_{1-4}$ alkoxy, which may optionally be partially or fully halogenated, halogen, methoxycarbonyl, phenylsulfonyl and —SO$_2$—CF$_3$;

$R^b$ is chosen from hydrogen, $C_{1-5}$ alkyl, $C_{2-5}$ alkenyl, $C_{2-5}$ alkynyl, $C_{3-8}$ cycloalkyl$C_{0-2}$ alkyl, aryl, $C_{1-5}$ alkoxy, $C_{1-5}$ alkylthio, amino, $C_{1-5}$ alkylamino, $C_{1-5}$ dialkylamino, $C_{1-5}$ acyl, $C_{1-5}$ alkoxycarbonyl, $C_{1-5}$ acyloxy, $C_{1-5}$ acylamino, $C_{1-5}$ sulphonylamino, hydroxy, halogen, trifluoromethyl, nitro, nitrile, or $R^b$ is chosen from heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl; and R[7] is hydrogen.

5. The compound according to claim 4 and wherein:

Y is —O— or —S—;

X is —N(R[a])— or —O—;

each R[3], R[4] and R[5] are hydrogen;

R[b] is chosen from hydrogen, $C_{1-5}$ alkyl, $C_{2-5}$ alkenyl, $C_{2-5}$ alkynyl, $C_{3-8}$ cycloalkyl$C_{0-2}$ alkyl, aryl, $C_{1-5}$ alkoxy, $C_{1-5}$ alkylthio, amino, $C_{1-5}$ alkylamino, $C_{1-5}$ dialkylamino, $C_{1-5}$ acyl, $C_{1-5}$ alkoxycarbonyl, $C_{1-5}$ acyloxy, $C_{1-5}$ acylamino, $C_{1-5}$ sulphonylamino, hydroxy, halogen, trifluoromethyl, nitro, nitrile or R[b] is chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

6. The compound according to claim 5 and wherein:

R[6] is present, and is chosen from a bond, —O—, —O—$(CH_2)_{1-5}$—, —NH—, —C(O)—NH—, $C_{1-5}$ alkyl branched or unbranched, $C_{2-5}$ alkenyl, $C_{1-3}$ alkyl(OH), heterocycle selected from morpholinyl, piperazinyl, piperidinyl, pyrrolidinyl and tetrahydrofuranyl, or aryl chosen from phenyl and naphthyl, each alkyl, alkenyl, heterocycle and aryl are optionally substituted by one to three hydroxy, $C_{1-3}$ alkyl, $C_{1-3}$ alkoxy, mono or di$C_{1-3}$ alkyl amino, amino or $C_{1-5}$ alkoxycarbonyl;

wherein each R[6] is further optionally covalently attached to groups chosen from:

hydrogen, NR[7]R[8], $C_{1-3}$ alkyl, $C_{3-6}$ cycloalkyl$C_{0-2}$alkyl, hydroxy, $C_{1-3}$ alkoxy, phenoxy, benzyloxy, phenyl$C_{0-4}$ alkyl, piperazinyl$C_{0-4}$ alkyl, piperidinyl $C_{0-4}$alkyl, pyrrolidinyl$C_{0-4}$ alkyl, morpholinyl$C_{0-4}$ alkyl, tetrahydrofuranyl$C_{0-4}$ alkyl, triazolyl $C_{0-4}$alkyl, imidazolyl $C_{0-4}$alkyl and pyridinyl $C_{0-4}$alkyl, each above listed heterocycle, heteroaryl and phenyl group is optionally substituted by one to three hydroxy, oxo, $C_{1-4}$ alkyl, $C_{1-3}$ alkoxy, $C_{1-5}$ alkoxycarbonyl, —NR[7]R[8], NR[7]R[8]—C(O)— or $C_{1-4}$ acyl;

each R[7] and R[8] are independently hydrogen, phenyl$C_{0-3}$alkyl optionally substituted by halogen, $C_{1-3}$ alkyl or di$C_{1-5}$ alkyl amino, or R[7] and R[8] are $C_{1-2}$ acyl, benzoyl or $C_{1-5}$ branched or unbranched alkyl optionally substituted by $C_{1-4}$ alkoxy, hydroxy or mono or di$C_{1-3}$ alkyl amino.

7. The compound according to any one of claims 1-6 and wherein:

if Ar[1] is (i), then Ar[1] is:

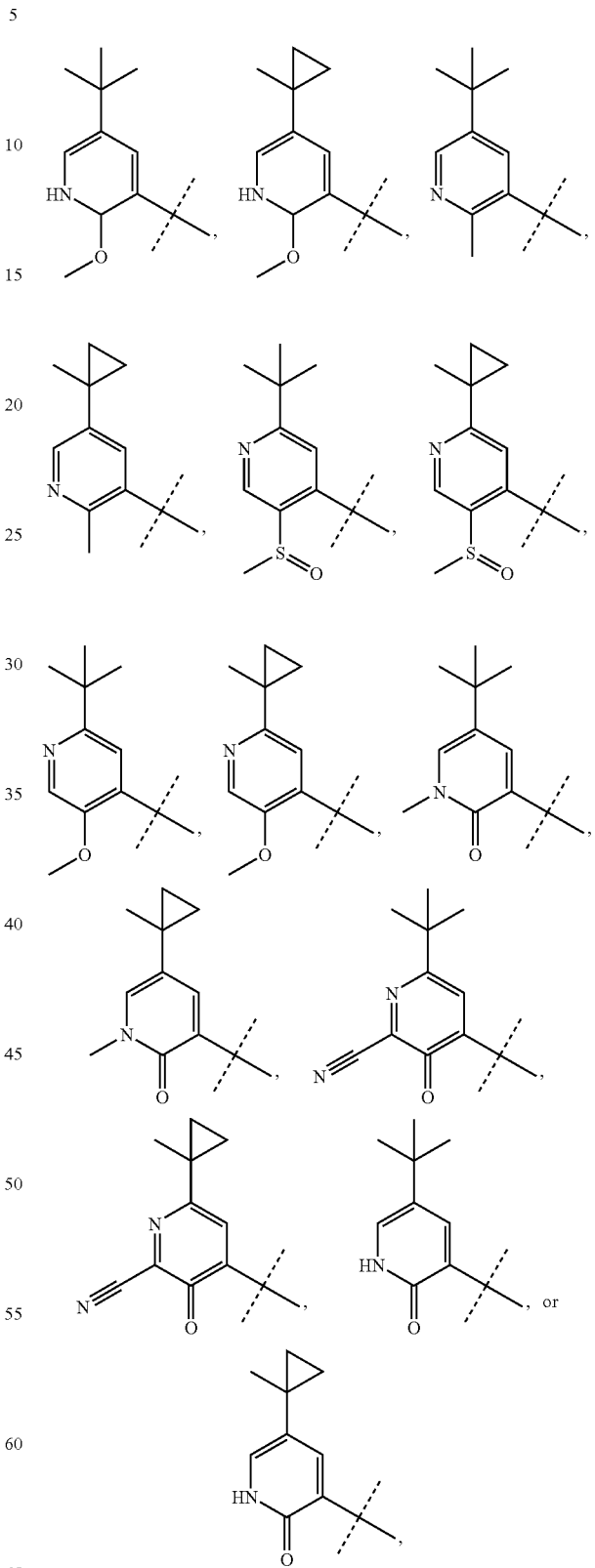

if Ar¹ is (ii), then Ar¹ is:
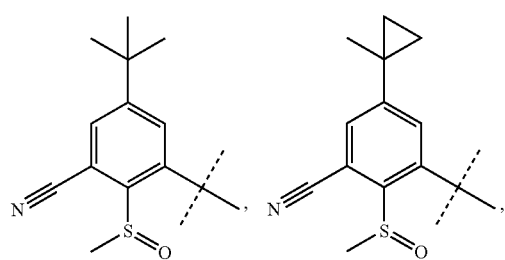
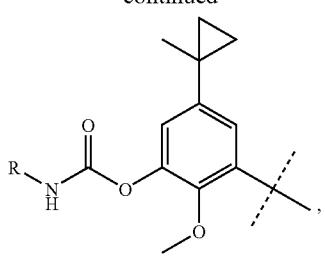
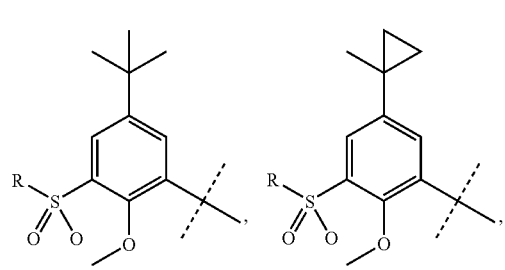
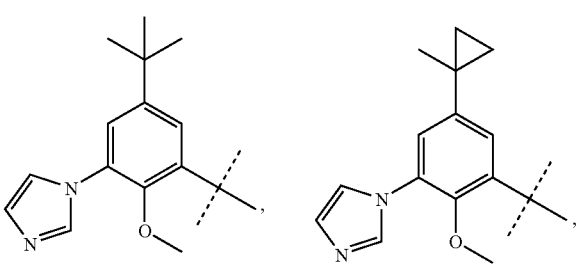
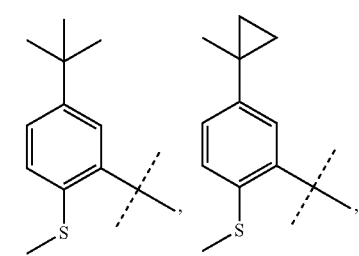
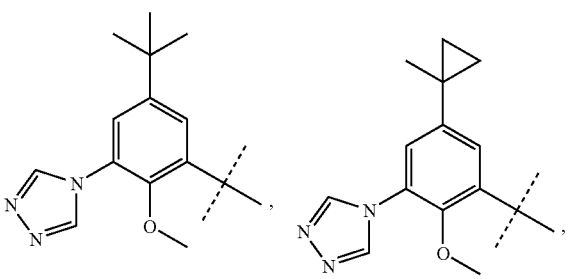
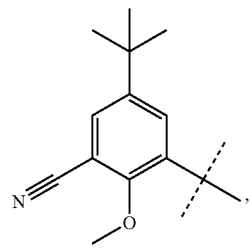
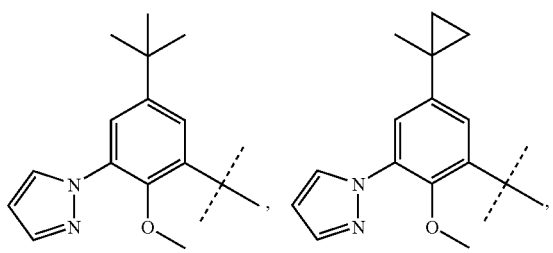
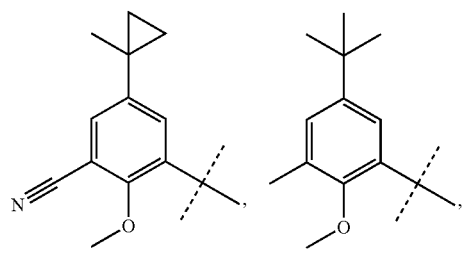
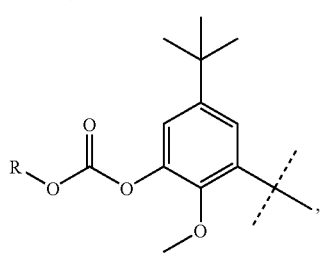
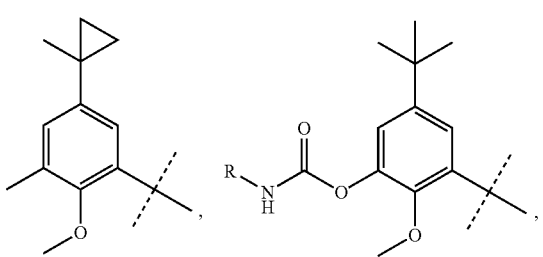
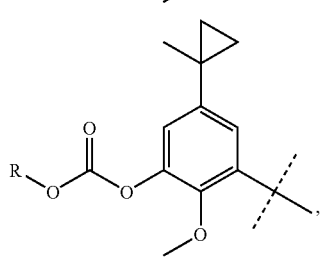

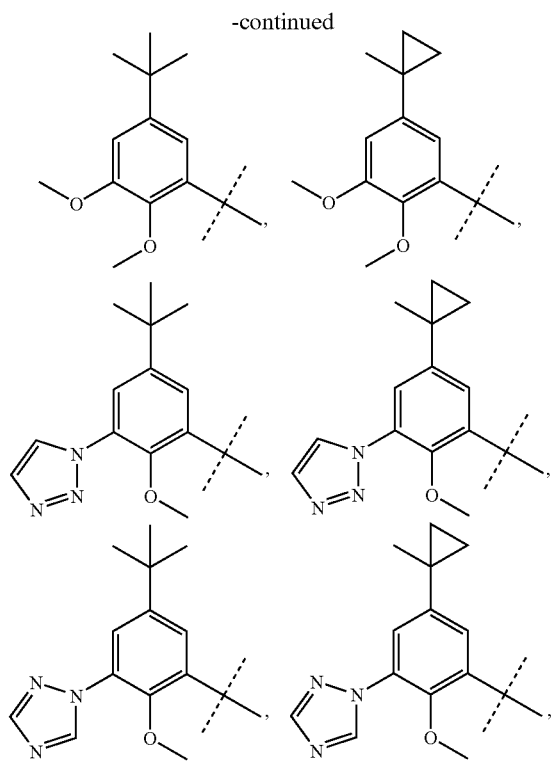
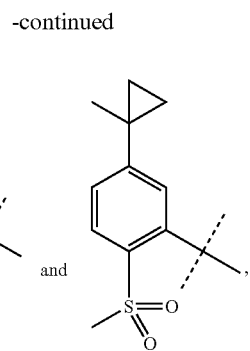
where R in these structures is $C_{1-5}$alkyl.
8. A pharmaceutical composition containing a pharmaceutically effective amount of a compound according to claim 1 and one or more pharmaceutically acceptable carriers and/or adjuvants.
\* \* \* \* \*